(12) United States Patent
Hanashi et al.

(10) Patent No.: US 9,488,578 B2
(45) Date of Patent: *Nov. 8, 2016

(54) SINGLE PARTICLE DETECTION DEVICE, SINGLE PARTICLE DETECTION METHOD, AND COMPUTER PROGRAM FOR SINGLE PARTICLE DETECTION, USING OPTICAL ANALYSIS

(71) Applicant: OLYMPUS CORPORATION, Tokyo (JP)

(72) Inventors: Takuya Hanashi, Hachioji (JP); Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,142

(22) Filed: Jan. 23, 2014

(65) Prior Publication Data
US 2014/0134608 A1    May 15, 2014

Related U.S. Application Data

(63) Continuation of application No. PCT/JP2012/063139, filed on May 23, 2012.

(30) Foreign Application Priority Data

Aug. 26, 2011    (JP) ................. 2011-184635

(51) Int. Cl.
*G01N 21/64* (2006.01)
*G01N 15/14* (2006.01)
(Continued)

(52) U.S. Cl.
CPC .............. *G01N 21/64* (2013.01); *G01N 15/14* (2013.01); *G01N 15/1429* (2013.01);
(Continued)

(58) Field of Classification Search
None
See application file for complete search history.

(56) References Cited

U.S. PATENT DOCUMENTS

| 4,251,733 A | 2/1981 | Hirleman, Jr. |
| 5,308,990 A | 5/1994 | Takahashi et al. |

(Continued)

FOREIGN PATENT DOCUMENTS

| CN | 101503734 A | 8/2009 |
| EP | 1 906 172 A1 | 4/2008 |

(Continued)

OTHER PUBLICATIONS

English translation of Written Opinion by ISA of International Application No. PCT/JP2013/056600 (Form PCT/ISA/237) mailed Jun. 18, 2013 with ISR (Form PCT/ISA/210) (6 pages).

(Continued)

*Primary Examiner* — Kara E Geisel
*Assistant Examiner* — Amanda Merlino
(74) *Attorney, Agent, or Firm* — Westerman, Hattori, Daniels & Adrian, LLP

(57) ABSTRACT

There is provided a single particle detection technique based on a scanning molecule counting method, enabling individual detection of a single particle using light measurement with a confocal or multiphoton microscope, and quantitative observation of conditions or characteristics of the particle. The inventive technique of detecting a single particle in a sample solution detects light containing substantially constant background light from a light detection region with moving the position of the light detection region of the microscope in a sample solution to generate time series light intensity data; and detects individually a light intensity reduction occurred when a single particle which does not emit light (or a particle whose emitting light intensity in a detected wavelength band is lower than the background light) enters in the light detection region in the time series light intensity data as a signal indicating the existence of each single particle.

33 Claims, 7 Drawing Sheets

(51) Int. Cl.
*G01N 21/51* (2006.01)
*G02B 21/00* (2006.01)

(52) U.S. Cl.
CPC ......... *G01N 15/1434* (2013.01); *G01N 21/51* (2013.01); *G01N 21/645* (2013.01); *G01N 21/6408* (2013.01); *G01N 21/6452* (2013.01); *G01N 21/6458* (2013.01); *G02B 21/008* (2013.01); *G02B 21/0032* (2013.01); *G02B 21/0076* (2013.01)

(56) References Cited

U.S. PATENT DOCUMENTS

| | | | |
|---|---|---|---|
| 5,319,575 A * | 6/1994 | Lilienfeld | 702/26 |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 8,284,484 B2 | 10/2012 | Hoult et al. | |
| 8,471,220 B2 * | 6/2013 | Yamaguchi et al. | 250/458.1 |
| 8,541,759 B2 * | 9/2013 | Yamaguchi et al. | 250/458.1 |
| 8,680,485 B2 | 3/2014 | Tanabe | |
| 8,710,413 B2 * | 4/2014 | Yamaguchi et al. | 250/203.3 |
| 9,068,944 B2 * | 6/2015 | Tanabe | |
| 9,188,535 B2 | 11/2015 | Hanashi | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2005/0130122 A1 | 6/2005 | Aravanis et al. | |
| 2005/0260660 A1 | 11/2005 | van Dongen et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2008/0052009 A1 | 2/2008 | Chiu et al. | |
| 2008/0067133 A1 | 3/2008 | Bryant et al. | |
| 2008/0158561 A1 | 7/2008 | Vacca et al. | |
| 2009/0159812 A1 | 6/2009 | Livingston | |
| 2010/0033718 A1 | 2/2010 | Tanaami | |
| 2010/0177190 A1 | 7/2010 | Chiang et al. | |
| 2010/0202043 A1 | 8/2010 | Ujike | |
| 2013/0302906 A1 | 11/2013 | Tanabe | |
| 2014/0134608 A1 | 5/2014 | Hanashi et al. | |
| 2015/0218628 A1 | 8/2015 | Hanashi | |

FOREIGN PATENT DOCUMENTS

| | | |
|---|---|---|
| EP | 2840381 A1 | 2/2015 |
| JP | 04-337446 A | 11/1992 |
| JP | 2002-507762 A | 3/2002 |
| JP | 2002318188 A | 10/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008523376 A | 7/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-002415 A | 1/2011 |
| JP | 2011-508219 A | 3/2011 |
| WO | 98/16814 A1 | 4/1998 |
| WO | 99/47963 A | 9/1999 |
| WO | 00/66985 A1 | 11/2000 |
| WO | 00/71991 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/106322 A1 | 9/2009 |
| WO | 2009/117033 A2 | 9/2009 |
| WO | 2010-119098 A1 | 10/2010 |
| WO | 2011/108369 A1 | 9/2011 |
| WO | 2011/108370 A1 | 9/2011 |
| WO | 2011/108371 A1 | 9/2011 |
| WO | 2012/039352 A1 | 3/2012 |
| WO | 2012-039352 A1 | 3/2012 |
| WO | 2013/031309 A1 | 3/2013 |

OTHER PUBLICATIONS

Extended European Search Report dated Oct. 20, 2014, issued in related EP Application No. 12770835.2 (10 pages).
Kinjo, Masataka, "Single molecule protein, nucleic acid, and enzyme assays and their procedures; Single molecule detection by fluorescence correlation spectroscopy", Proteins, Nucleic Acids and Enzymes, 1999, vol. 44, No. 9, pp. 1431-1438, w/ English translation.
Meyer-Almes, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224.
Katoh, Noriko et al., "A single molecule analyzer that enable new analysis of DNA and protein interaction", Genetic Medicine, 2002, vol. 6, No. 2, pp. 271-277.
P. Kask et al., "Fluorescence-intensity distribution analysis and its application in biomolecular detection technology", PNAS, Nov. 23, 1999, vol. 96, No. 24, pp. 13756-13761.
International search Report for PCT/JP2012/063139, Mailing Date of Jul. 24, 2012.
U.S. Office Action dated Feb. 9, 2015, issued in U.S. Appl. No. 14/496,177 (7 pages).
Related co-pending U.S. Appl. No. 14/496,177.
Related co-pending U.S. Appl. No. 14/465,208.
SupplementaryEuropean Search Report dated Apr. 23, 2015, issued in related European Patent Application No. 12828640.8 (16 pages).
Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, (p. 1612-1618).
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, (p. 1703-1713).
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483, Mar. 30, 2012.
Chinese Office Action dated Aug. 9, 2013, issued in related Chinese application No. 201180011640.7; w/ English Translation (16 pages).
International Search Report Mar. 29, 2011, issued in related PCT/JP2011/053482.

(56) References Cited

OTHER PUBLICATIONS

International Preliminary Report on Patentability (PCT/IPEA/409) issued in related PCT/JP2011/053482 Mar. 3, 2012.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481, Jun. 15, 2012.
Goodwin, Peter et al., "Rapid Sizing of Individual Fluorescently Stained DNA Fragments by Flow Cytometry," Nucleic Acids Research, 1993, vol. 21, No. 4 (p. 803-806).
Keller, Richard et al., "Single-Molecule Fluorescence Analysis in Solution," Applied Spectroscopy, 1996, vol. 50, No. 7, (p. 12A-32A).
Lee, Yuan-Hsiang et al., "Laser-Induced Fluorescence Detection of a Single Molecule in a Capillary," Analytical Chemistry, dated Dec. 1, 1994, vol. 66, No. 23, (p. 4142-4149).
Li, Haitao et al., "Ultrasensitive Coincidence Fluorescence Detection of Single DNA Molecules," Analytical Chemistry, dated Apr. 1, 2003, vol. 75, No. 7, (p. 1664-1670).
Nie, Shuming et al., "Probing Individual Molecules with Confocal Fluorescence Microscopy," Science, dated Nov. 11, 1994, vol. 266, (p. 1018-1021).
Tahari, Abdel. "Fluorescence Correlation Spectroscopy: Ultrasensitive Detection in Clear and Turbid Media," University of Illinois, 2006, (p. 1-88).
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, (p. 2157-2159).
Itoh et al., "A New Method for Detection of Influenza Viruses by Single Particle-Recognition Based on the Principle of Fluorescence Correlation Spectroscopy," Chemistry and Biology, 2009, vol. 47, No. 12, (p. 823-830).
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Apr. 16, 2013, issued in related PCT/JP2013/050025.
International Search Report dated Jun. 18, 2013, issued in related PCT/JP2013/056600.
International Search Report dated Nov. 29, 2011, issued in related PCT/JP2011/072939.
International Search Report for PCT/JP2013/068406, mailing date of Oct. 15, 2013.
International Search Report for PCT/JP2013/052110, mailing date of May 7, 2013.
Extended European Search Report dated Oct. 26, 2015, issued in counterpart European Patent Application No. 13777928.6 (7 pages).
Wennmalm et al., "Inverse-Fluorescence Cross-Correlation Spectroscopy," Analytical Chemistry, vol. 82, No. 13, Jul. 1, 2010, pp. 5646-5651 (6 pages).
Final Office Action dated Sep. 29, 2015, issued in U.S. Appl. No. 13/946,091 (23 pages).
Final Office Action dated Sep. 28, 2015, issued in U.S. Appl. No. 13/746,968 (24 pages).
Office Action dated Jun. 1, 2015, issued in counterpart Chinese Patent Application No. 201280041717.X, w/English translation (26 pages).
With English translation of Chinese Office Action dated Dec. 2, 2015, issued in related Chinese Patent Application No. 201380020726.5.
Office Action dated Jan. 27, 2016, issued in Chinese Patent Application No. 201280041717.X, w/English translation.
Office Action dated Mar. 22, 2016, issued in Japanese Patent Application No. 2013-531130, w/English translation.
U.S. Notice of Allowance dated Mar. 27, 2013, issued in related U.S. Appl. No. 13/597,825 (8 pages).
U.S. Non-Final Office Action dated May 11, 2016, issued in U.S. Appl. No. 14/465,208.
Extended (Supplementary) European Search Report (EESR) dated May 27, 2016, issued in counterpart European Patent Application No. 13849687.2. (6 pages).
Chinese Office Action dated Aug. 3, 2016, issued in related Chinese application No. 201280041717.X; with English Translation.

* cited by examiner

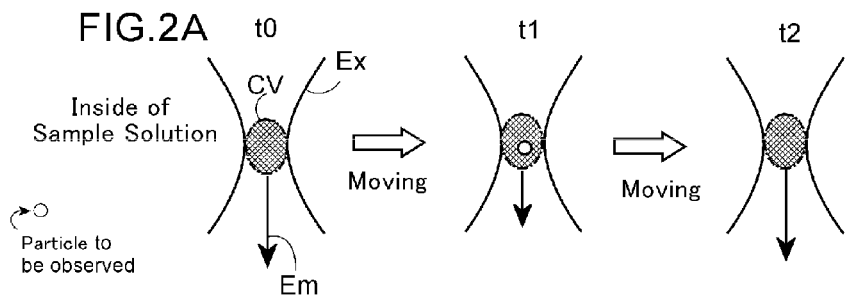
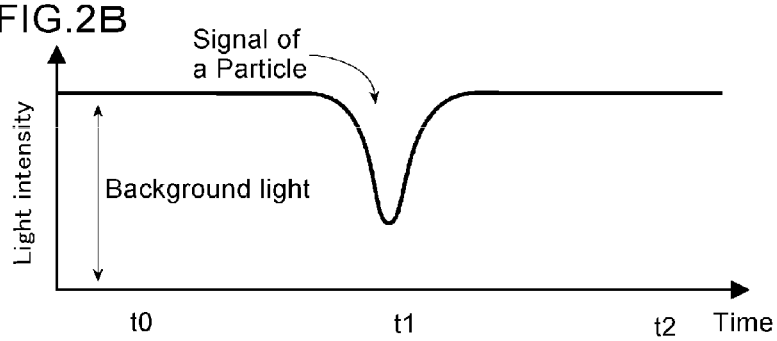
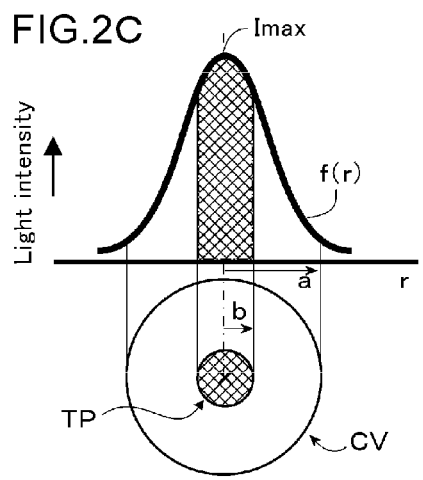
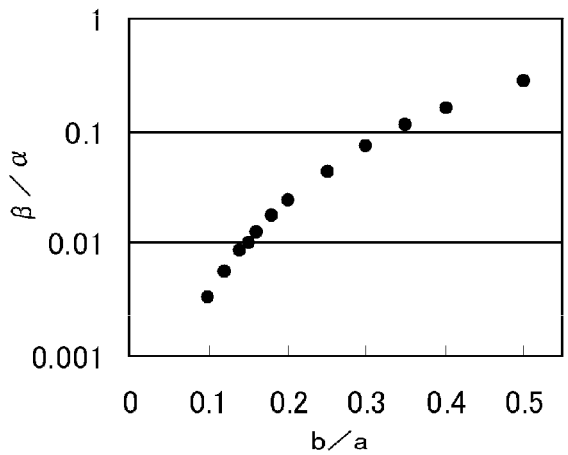

FIG.4A
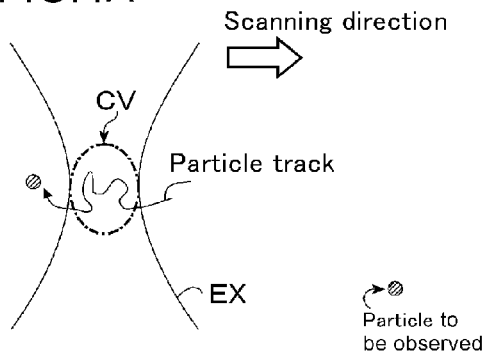
FIG.4B
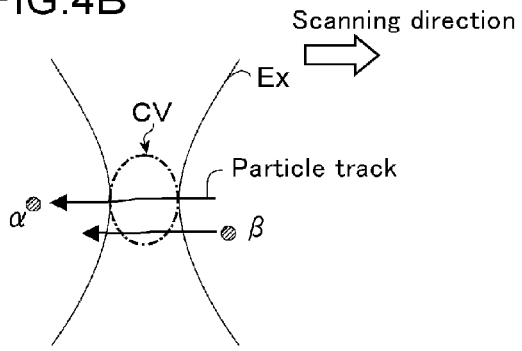
FIG.4C
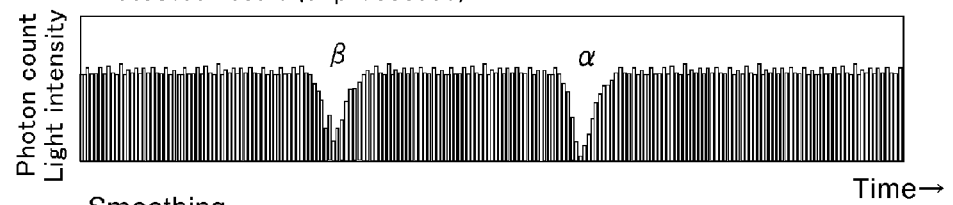
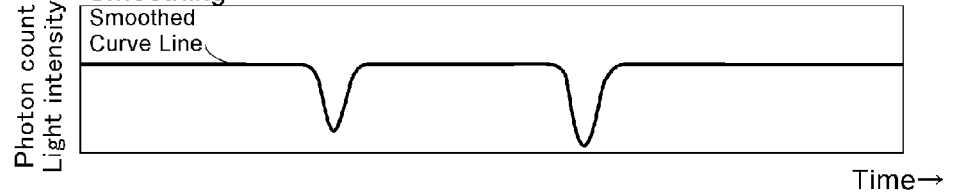
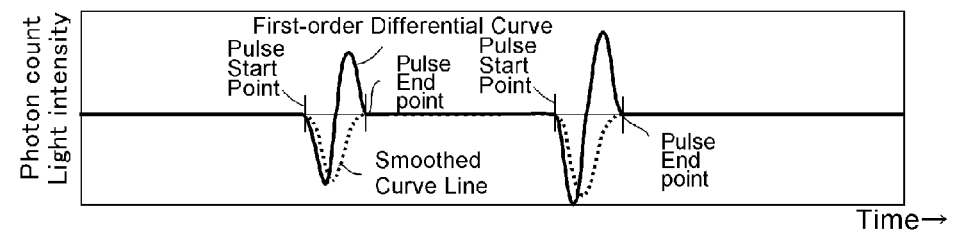
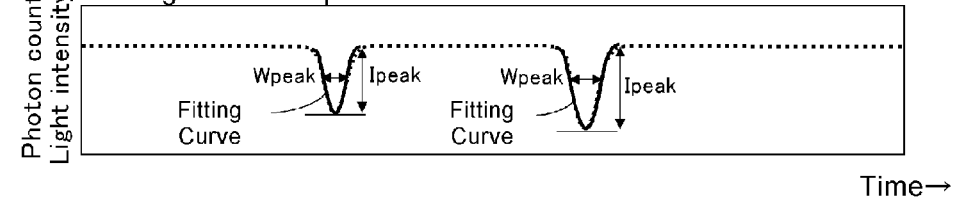

SINGLE PARTICLE DETECTION DEVICE, SINGLE PARTICLE DETECTION METHOD, AND COMPUTER PROGRAM FOR SINGLE PARTICLE DETECTION, USING OPTICAL ANALYSIS

TECHNICAL FIELD

This invention relates to a single particle detection technique capable of detecting a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a single particle detection device, a single particle detection method and a computer program for single particle detection, measuring with an optical system as described above a light intensity change because of an existence of a single particle to detect a single particle, and thereby enabling various analyses.

BACKGROUND ART

According to the developments in optical measurement techniques in recent years, detection and/or measurement of faint light at the single photon or single fluorescent molecule level have become possible by using an optical system of a confocal microscope and a super high sensitive light detection technique capable of the photon counting (single photon detection). Thus, there are variously proposed devices or methods of detecting single particles by means of such a faint light measurement technique to perform detection of a characteristic, an intermolecular interaction, a binding or dissociating reaction of a biological molecule, etc. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate. Moreover, patent documents 9 has disclosed, as one manner of FCS, a method, wherein, in a system of a solution which contains a lot of dissolved light-emitting substances so that the entry of a non-light-emitting particle, dispersed in the solution, into a confocal volume will cause the reduction of detected light intensity, the translational diffusion time in the confocal volume and the average of dwelling particle counts of non-light-emitting particles are computed through computation of the autocorrelation function value of the fluorescence intensity (inverted FCS (iFCS)).

According to the methods employing the measurement technique of fluorescent light of a micro region using the optical system of a confocal microscope and a photon counting technique as described above, such as FCS and FIDA, a sample amount required for the measurement may be extremely small (an amount used in one measurement is at most several tens of µL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent documents 9: WO 2010-119098

Non-Patent Documents

Non-patent document 1: Masataka Kaneshiro; "Protein, Nucleic acid, Enzyme" Vol. 44, No. 9, pages 1431-1438, 1999.

Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the analysis technique using the optical system of a confocal microscope and a photon counting technique, such as FCS and FIDA, as described above, although an observation of behaviors of single particles is conducted using change of the light intensity at a level of single or several fluorescent molecules, there are conducted in the analysis of the light intensity the statistical procedures for the calculating of the fluorescence intensity fluctuation, etc., such as the computation of the autocorrelation function or the fitting to the histogram of fluorescence intensity data measured in time series, and therefore the behavior of an individual single particle is not seen or analyzed. That is, in these analysis techniques, through the statistical processing of the light intensity variations indicating the existences of particles, statistical average characteristics of the particles will be detected. Thus, in order to obtain a statistically significant result in these analysis techniques, the concentration or number density of a single particle to be an observation object in the sample solution should be at such a level that single particles of the number enabling a statistical process will enter in and exit from a micro region in one measuring term of a length of order of seconds in an equilibrium, preferably at such a level that about one single particle will be always present in the micro region. Actually, since the volume of a confocal volume is about 1 fL, the concentration of a single particle in a sample solution used in the above-mentioned optical analysis technique is typically at the level of 1 nM or more, and at much less than 1 nM, there is produced a term in which no single particles are present in the confocal volume so that no statistically significant analysis result will be obtained. On the other hand, in the detection methods of single particles described in patent documents 6-8, no statistical computation processes of fluorescence intensity fluctuation are included so that a single particle even at less than 1 nM in a sample solution can be detected, but, it has not been achieved to compute quantitatively the concentration or number density of a single particle moving at random in a solution.

Then, in Japanese patent application No. 2010-044714 and PCT/JP2011/53481. Applicant of the present application has proposed an optical analysis technique based on a new principle which makes it possible to observe quantitatively a condition or characteristic of a particle emitting light to be an observation object (light-emitting particle) in a sample solution where the concentration or number density of the light-emitting particle is lower than the level at which the analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 µL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the scanning molecule counting method which detects individually the light of a single particle emitting light as described above, since the light from a single particle is weak, it is liable to be affected by the influence of stray light or Raman scattering light of water. Accordingly, in the case of the analytical way of identifying an increase of the light intensity value indicating the light emitted from a light-emitting particle as a signal of the light-emitting particle, it is possible that the light owing to stray light or Raman scattering light of water is erroneously identified as a signal of a light-emitting particle. Further, in the case of the scanning molecule counting method detecting the light of a single particle, the particle to be an observation object (particle to be observed) is limited to a light-emitting particle. Thus, in order to observe a particle which does not emit light, it is required to give a light emitting label (a fluorescent indicator, a phosphorescent indicator, etc.) to the particle to be the observation object; however, it is not always possible to attach an adequate light emitting label to the particle to be observed (Denaturalization of a particle to be observed may occur due to the attaching of a light emitting label.).

Thus, the main object of the present invention is to provide a scanning molecule counting method which is not liable to be affected by influences of stray light or Raman scattering light of water and enables the observation of a particle which does not emit light, namely, a single particle detection technique according to a new principle which makes it possible to detect individually a single particle which does not emit light in a sample solution and to observe the condition or characteristic of the particle quantitatively.

In this regard, in conducting an optical measurement with an optical system of a microscope, generally, it is less liable to be affected by the influences of stray light or Raman scattering light of water when background light is high. Further, because, in the optical system of confocal microscopes or multiphoton microscopes, the resolution in the direction of the optical axis is higher than usual light microscopes, the reduction of the light intensity from the confocal volume can be observed when a single particle which does not emit light passes through the confocal volume (patent documents 9). This knowledge is used in the present invention.

Solution to Problem

According to one aspect of the present invention, the above-mentioned object is achieved by a single particle detection device which detects light from a single particle dispersed and moving at random in a sample solution using an optical system of a confocal microscope or a multiphoton microscope, comprising: a light detection region mover which moves a position of a light detection region of the optical system of the microscope in the sample solution; a light detector which detects light from the light detection region; and a signal processor which generates time series light intensity data of the light from the light detection region detected with the light detector with moving the position of the light detection region in the sample solution and detects a signal indicating the existence of each single particle individually in the time series light intensity data; wherein the light from the light detection region includes substantially constant background light; and the signal indicating an existence of each single particle is a reduction of the light intensity detected with the light detector, which reduction occurs when the single particle enters into the light detection region. In this structure, "a single particle particle dispersed and moving at random in a sample solution" may be a single particle, such as an atom, a molecule or an aggregate of these, which is dispersed or dissolved in a sample solution, and it may be an arbitrary particulate matter making the Brownian motion freely in a solution without being fixed on a substrate, etc. Further, the single particle to be an object to be observed in the present invention may be a particle which significantly reduces the light amount from the light detection region when the particle exists in the light detection region, and thus, basically it is a single particle which does not emit light, but, it should be understood that it may be a particle whose emitting light intensity is lower than the background light in the detected light wavelength band. The "light detection region" of the optical system of the confocal microscope or multiphoton microscope is the micro region where light is detected in those microscopes, which region corresponds to the region to which illumination light is condensed when the illumination light is given from an objective (Especially in the confocal microscope, this region is determined in accordance with the spatial relationship of an objective and a pinhole.). Further, in the followings in this specification, "a signal of a single particle" means "a signal indicating the existence of a single particle" unless noted otherwise.

As understood from the above, in the inventive device, similarly to the "scanning molecule counting method" described in the patent applications JP2010-044714 and PCT/JP2011/53481, the detection of light is sequentially performed with moving the position of the light detection region in the sample solution, i.e., with scanning the inside of the sample solution with the light detection region. In this structure, in a case that constant background light is substantially included in the light from the light detection region, when a single particle enters into the light detection region or when the light detection region moving within the sample solution encompasses a single particle, the light intensity or the light amount of the background light which reaches from the light detection region to the light detector is reduced because of the existence of the single particle. Thus, in the inventive device, such a reduction of the light intensity or light amount of the background light is individually detected as a signal of a single particle in the sequentially detected light, and thereby, the existences of particles is sequentially and individually detected, so that diverse information on the conditions of particles in the solution will be acquired. That is, in the inventive device, a single particle is detected individually by detecting the shadow of a single particle in the region where the background light exists. According to this structure, even in a case that a single particle to be an observation object emits no light or its emitting light intensity is low, it is not necessary to give a light emitting label to the single particle, and also, erroneous judgments of stray light and Raman scattering light as a signal of a particle to be observed are avoided.

In the above-mentioned inventive device, the substantially constant background light to be included in the light from the light detection region may be fluorescence, phosphorescence, chemiluminescence, bioluminescence, or scattered light by substance dispersed in the sample solution. In this case, when no substance emitting or scattering light is dispersed in a solution used as a sample solution, substance emitting or scattering light may be dissolved or dispersed into this solution positively. Further, when a solution used as a sample solution emits autofluorescence, the autofluorescence may be used as the above-mentioned background light. Especially when substance producing background light needs excitation light or illumination light, the microscope device is equipped with a light source and an optical system for the illumination light. On the other hand, in a case that substance producing background light emits light without excitation light or illumination light, for example, in a case of substance emitting light according to chemiluminescence or bioluminescence, no illumination light is required in the microscope device. Furthermore, it should be understood that the background light may be illumination light by transmitted illumination, etc. if it is reduced when a single particle exists in the light detection region. In this connection, in the above mentioned inventive structure, where a background light reduction because of the existence of a single particle is detected, the degree of the background light reduction depends on the relation between the size of the single particle and the size of the light detection region. In this respect, according to the estimations described in detail later, it has been found that, preferably, the outer diameter of a single particle to be an observation object is not less than 15% of diameter of the light detection region, and more preferably, the outer diameter of a single particle to be an observation object is not less than 35% of diameter of the light detection region.

In the above-mentioned inventive device, the moving speed of the position of the light detection region in the sample solution may be appropriately changed based on the characteristics, number density or concentration of the single particle in the sample solution. Especially when the moving speed of the light detection region becomes quick, the degree of reduction of the light intensity or light amount because of the existence of a single particle will decrease, and thus, in order to make it possible to precisely and sensitively measure a reduction of the light intensity or light amount because of a single particle, it is preferable that the moving speed of the light detection region is changeable appropriately.

Furthermore, the moving speed of the position of the light detection region in the sample solution is preferably set to be higher than the diffusional moving velocity of a single particle to be a detected object (the average moving speed of a particle owing to the Brownian motion). As explained above, in the inventive device, a single particle will be detected individually by detecting a background light reduction because of the existence of the single particle when the light detection region passes through the existence position of the single particle. However, when the single particle moves at random owing to the Brownian motion to move into and out of the light detection region multiple times, it is possible that the signal from one single particle showing its existence will be detected multiple times, and therefore it would become difficult to make the existence of one single particle associated with the detected signal. Then, as described above, the moving speed of the light detection region is set higher than the diffusional moving velocity of a single particle, and thereby it becomes possible to make one light-emitting particle correspond to one signal (indicating the single particle). In this regard, since the diffusional moving velocities differ depending upon characteristics of single particles, preferably, the inventive device is so designed that the moving speed of the light detection region can be changed appropriately according to the characteristics (especially, the diffusion constant) of the single particle as described above.

The moving of the position of the light detection region may be done in an arbitrary way. For example, the position of the light detection region may be changed by changing the optical path, such as by using a galvanomirror employed in a laser scan type optical microscope, or the relative position of the light detection region in the sample solution may be moved by moving the position of the sample solution, such as by moving the stage of the microscope. The movement track of the position of the light detection region may be set arbitrarily, for example, which is selectable from circular, elliptical, rectangular, straight and curvilinear ones. Especially, in the case that the position of the light detection region is moved by changing the optical path of the optical system of the microscope, it is advantageous in that the movement of the light detection region is quick without substantial generation of mechanical vibration and hydrodynamic effect in the sample solution, and therefore, the measurement of light can be performed under a stable condition without dynamic action affecting the single particle to be an object to be detected in the sample solution.

Moreover, in the process of the signal processor of the above-mentioned inventive device, the judgment of whether or not one particle has entered into the light detection region by means of signals of successive detected values from the light detector may be done based on the shapes of the time series signals indicating light detected in the light detector. In an embodiment, typically, when a signal whose light intensity is lower than a predetermined threshold value measured from the background light intensity is detected, it may be judged that one single particle has entered into the light detection region. More concretely, as explained in the column of the embodiments later, usually, in the detected value of the time series of a light detector, i.e., light intensity data, a signal indicating the existence of a single particle appears as a downwardly convex, bell-shaped pulse form signal descending to a certain degree of intensity, and a noise appears in non bell-shaped pulse form or as a high intensity one. Then, the signal processor of the inventive device may be designed to detect a downwardly convex, pulse form bell shaped signal descending below a predetermined threshold value measured from a background light intensity as a signal indicating the existence of a single particle in time series light intensity data. The "predetermined threshold value" can be experimentally set to an adequate value.

Furthermore, the light intensity obtained by the inventive device is comparatively weak, in which small increases and decreases, causing deterioration of the detection accuracy of a signal indicating the existence of a single particle, are generated. Thus, the signal processor may be designed to conduct the smoothing of the time series light intensity data for processing the data where small increases and decreases in the light intensity can be disregarded, and then to detect in the smoothed time series light intensity data a downwardly convex bell-shaped pulse form signal whose intensity descends below a predetermined threshold value measured from the background light intensity as a signal indicating the existence of a single particle.

In one of manners of the above-mentioned present invention, the number of single particles encompassed in the light detection region may be counted by counting the number of the selectively detected signals (The counting of particles). In that case, by associating the number of the detected single particles with the moving amount of the position of the light detection region, the information on the number density or concentration of the single particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the single particle can be concretely computed.

By the way, in a typical manner of counting of particles, the number of the signals of single particles obtained in the measuring time set arbitrarily is counted. In that case, however, the number of the detected signals of the single particles changes with the length of the set measuring time, and especially, in a case of a low single particle concentration, the scattering of the single particle concentration values computed from the numbers of detected signals becomes large, so that its accuracy would be reduced. Thus, in the above-mentioned inventive device, as another manner of the counting of particles, the measurement may be performed until the number of signals of single particles reaches the arbitrarily set number, and based on its measuring time, the single particle concentration value may be computed. Namely, the above-mentioned inventive device may be designed to repeat the moving of the position of the light detection region of the optical system by the light detection region mover, the detecting of the light from the light detection region by the light detector and the detecting of the signals indicating the existences of the single particle by the signal processor until the number of the signals indicating the existences of the single particles detected with the signal processor reaches a predetermined number; and to determine a concentration of the single particle in the sample solution based on the time taken for the number of the signals indicating the existences of the single particles to reach the predetermined number. In this case, the shortening of the measuring time for a sample solution of a high single particle concentration is expected, and the measurement for a sample solution of a low single particle concentration will be performed with spending sufficient time. That is, according to the above-mentioned structure, the measuring time is optimized in accordance with the single particle concentrations. Moreover, when the predetermined number is set to the number which attains the accuracy requested for the result, the scatterings in the time taken for the detection of the predetermined number of the single particles and an arbitrary result derived therefrom can be suppressed, making the accuracy of the result(s) satisfactory.

The processes of the single particle detection technique of conducting the light detection in the presence of constant background light with moving the position of the light detection region in a sample solution, detecting individually a reduction of the light intensity or light amount of the background light as a signal of a single particle, thereby detecting sequentially and individually the existence of each particle in the above-mentioned inventive device can be realized with a general-purpose computer, also. Thus, according to another aspect of the present invention, there is provided a computer readable storage device having a computer program product including programmed instructions for single particle detection of detecting light from a light-emitting particle dispersed and moving at random in a sample solution using an optical system of a confocal microscope or a multiphoton microscope, said programmed instructions causing a computer to perform steps of: moving a position of a light detection region of the optical system of the microscope in the sample solution; detecting light including substantially constant background light from the light detection region with moving the position of the light detection region in the sample solution, and generating time series light intensity data; and detecting in the time series light intensity data individually a reduction of the light intensity occurring when the single particle has entered into the light detection region as a signal indicating an existence of each single particle. In the present application, "computer readable storage device" does not cover transitory propagating signal per se. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this structure, the background light may be fluorescence, phosphorescence, chemiluminescence, bioluminescence, scattered light owing to substances dispersed in the sample solution or illumination light. Further, the outer diameter of the single particle is preferably not less than 15% of the diameter of the light detection region, and more preferably not less than 35% of the diameter of the light detection region. As noted, the single particle to be an object to be observed is a particle which significantly reduces the light amount from the light detection region because of its existence in the light detection region, namely, a particle emitting no light or a particle whose emitting light intensity is lower than the background light in the detected light wavelength band.

Moreover, even in the above-mentioned computer readable storage device, the individual detection of a signal indicating the existence of each single particle may be done based on the shape of the time series signal. In an embodiment, typically, in the step of detecting the signal indicating the existence of the single particle individually, it may be judged that one single particle has entered into the light detection region when a signal whose light intensity is lower than a predetermined threshold value measured from the intensity of the background light is detected. Concretely, in the step of detecting the signal indicating the existence of the single particle individually, a downwardly convex, bell-shaped pulse form signal whose intensity is lower than a predetermined threshold value measured from the intensity of the background light in the time series light intensity data may be detected as the signal indicating the existence of the single particle, and in this case, the time series light intensity data may be smoothed and a downwardly convex, bell-shaped pulse form signal in the smoothed time series light intensity data may be detected as a signal indicating the existence of a single particle.

Furthermore, the moving speed of the position of the light detection region in the sample solution may be appropriately changed based on the characteristics, number density or concentration of the single particle in the sample solution, and preferably, the moving speed of the position of the light detection region in the sample solution is set higher than the diffusion moving velocity of the single particle to be an object to be detected. The moving of the position of the light detection region in the sample solution may be done by an arbitrary way, and preferably, the position of the light detection region may be changed by changing the optical path of the optical system of the microscope or by moving the position of the sample solution. The movement track of the position of the light detection region may be set arbitrarily, for example, which is selectable from circular, elliptical, rectangular, straight and curvilinear ones.

Further, the above-mentioned computer readable storage device may also comprise a step of counting a number of the signals indicating the existences of the single particles individually detected during moving the position of the light detection region to count a number of the single particles and/or a step of determining a number density or concentration of the single particle in the sample solution based on the number of the detected single particles. In this regard, also in the case of the above-mentioned computer readable storage device, typically, the counting of particles is conducted by counting the number of signals of single particles obtained in a arbitrarily set measuring time; however, the measurement may be performed until the number of signals of single particles reaches an arbitrarily set number, and the single particle concentration value may be computed based on the measuring time. Thus, the above-mentioned computer readable storage device may be designed to repeat until the number of the signals indicating the existences of the single particles detected with the signal processor reaches a predetermined number the moving of the position of the light detection region of the optical system by the light detection region mover, the detecting of the light from the light detection region by the light detector and the detecting of the signals indicating the existences of the single particle by the signal processor; and to determine a concentration of the single particle in the sample solution based on the time taken for the number of the signals indicating the existences of the single particles to reach the predetermined number.

According to the above-mentioned inventive device or computer readable storage device, there is realized a novel method of conducting the light detection in the presence of constant background light with moving the position of the light detection region in a sample solution, detecting individually a reduction of the light intensity or light amount of the background light as a signal of a single particle, thereby detecting sequentially and individually the existence of each particle one by one. Thus, according to the present invention, there is further provided a single particle detection method of detecting a single particle dispersed and moving at random in a sample solution using an optical system of a confocal microscope or a multiphoton microscope, comprising steps of: moving a position of a light detection region of the optical system in the sample solution; detecting light including substantially constant background light from the light detection region with moving the position of the light detection region in the sample solution, and generating time series light intensity data; and detecting in the time series light intensity data individually a reduction of the light intensity occurring when the single particle has entered into the light detection region as a signal indicating an existence of each single particle.

Also in this structure, the background light may be fluorescence, phosphorescence, chemiluminescence, bioluminescence, scattered light owing to substances dispersed in the sample solution or illumination light. Further, the outer diameter of the single particle is preferably not less than 15% of the diameter of the light detection region, and more preferably not less than 35% of the diameter of the light detection region. As noted, the single particle to be an object to be observed is a particle which significantly reduces the light amount from the light detection region because of its existence in the light detection region, namely, a particle emitting no light or a particle whose emitting light intensity is lower than the background light in the detected light wavelength band.

Moreover, even in the above-mentioned method, the individual detection of a signal indicating the existence of each single particle may be done based on the shape of the time series signal. In an embodiment, typically, in the step of detecting the signal indicating the existence of the single particle individually, it may be judged that one single particle has entered into the light detection region when a signal whose light intensity is lower than a predetermined threshold value measured from the intensity of the background light is detected. Concretely, in the step of detecting the signal indicating the existence of the single particle individually, a downwardly convex, bell-shaped pulse form signal whose intensity is lower than a predetermined threshold value measured from the intensity of the background light in the time series light intensity data may be detected as the signal indicating the existence of the single particle, and in this case, the time series light intensity data may be smoothed and a downwardly convex, bell-shaped pulse form signal in the smoothed time series light intensity data may be detected as a signal indicating the existence of a single particle.

Furthermore, the moving speed of the position of the light detection region in the sample solution may be appropriately changed based on the characteristics, number density or concentration of the single particle in the sample solution, and preferably, the moving speed of the position of the light detection region in the sample solution is set higher than the diffusion moving velocity of the single particle to be an object to be detected. The moving of the position of the light detection region in the sample solution may be done by an arbitrary way, and preferably, the position of the light detection region may be changed by changing the optical path of the optical system of the microscope or by moving the position of the sample solution. The movement track of the position of the light detection region may be set arbitrarily, for example, which is selectable from circular, elliptical, rectangular, straight and curvilinear ones.

Further, the above-mentioned method may also comprise a step of counting a number of the signals indicating the existences of the single particles individually detected during moving the position of the light detection region to count a number of the single particles and/or a step of determining a number density or concentration of the single particle in the sample solution based on the number of the detected single particles. In this regard, also in the case of the above-mentioned method, typically, the counting of particles is conducted by counting the number of signals of single particles obtained in a arbitrarily set measuring time; however, the measurement may be performed until the number of signals of single particles reaches an arbitrarily set number, and the single particle concentration value may be computed based on the measuring time. Thus, the above-mentioned method may be designed to repeat until the number of the signals indicating the existences of the single particles detected with the signal processor reaches a predetermined number the moving of the position of the light detection region of the optical system by the light detection region mover, the detecting of the light from the light detection region by the light detector and the detecting of the signals indicating the existences of the single particle by the signal processor; and to determine a concentration of the single particle in the sample solution based on the time taken for the number of the signals indicating the existences of the single particles to reach the predetermined number.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a liposome, metallic colloid, a bead (a magnetic bead, a polystyrene bead, a latex bead, etc.), a quencher (azobenzenes (dabcyl, BHQ, etc.), a metallic particle etc.), and it should be understood that such a case belongs to the scope of the present invention also.

Effect of Invention

Generally, the inventive single particle detection technique employs the principle of the scanning molecule counting method to enable the detection of a single particle which does not emit light (or a particle whose emitted light intensity is lower than background light in a detected light wavelength band) dispersed in the solution. Thus, its light detection mechanism itself is constituted to detect light from a light detection region of a confocal microscope or a multiphoton microscope similarly to the usual scanning molecule counting method, and therefore, the amount of a sample solution may be small similarly. However, since no statistical procedure of computing the fluorescence intensity fluctuation is performed in the present invention, the inventive single particle detection technique is applicable to a sample solution whose single particle number density or concentration is substantially lower than the level required in optical analysis techniques, such as FCS, FIDA and PCH. Moreover, according to this structure, it is not necessary to attach a light emitting label to a single particle, and thus, even a particle which is denaturalized by attaching a light emitting label thereto can be chosen as a particle to be observed. Furthermore, according to the manner of detecting, as a signal indicating the existence of a single particle, a background light reduction in the presence of a certain degree of background light, erroneous detections of stray light and Raman scattering light as a signal of a particle to be observed would be eliminated.

Other purposes and advantages of the present inventions will become clear by explanations of the following preferable embodiments of the present invention.

BRIEF DESCRIPTIONS OF DRAWINGS

FIG. 1A is a schematic diagram of the internal structure of a single particle detection device performing the inverted scanning molecule counting method in accordance with the present invention. FIG. 1 (B) is a schematic diagram of a confocal volume (a light detection region of a confocal microscope). FIG. 1 (C) is a schematic diagram of the mechanism for changing the direction of the mirror 7 to move the position of a light detection region in a sample solution. FIG. 1 (D) is a schematic diagram of the mechanism for moving the horizontal position of a micro plate to move the position of the light detection region in a sample solution.

FIGS. 2A and 2B are a schematic diagram explaining the principle of detecting the existence of a single particle and a schematic diagram of the variation of the measured light intensity with time in the inverted scanning molecule counting method of the present invention, respectively. FIG. 2C is a diagram explaining the principle of the reduction of the detected light amount at the time of a single particle entering into a light detection region, and FIG. 2D is a diagram showing the relation between the diameter ratios of a light detection region and a single particle and the ratios of a reduction of the detected light amount.

FIG. 3 is a diagram showing the procedures of the inverted scanning molecule counting method performed in accordance with the present invention in the form of a flow chart.

FIGS. 4A and 4B are drawings of models in a case that a single particle crosses a light detection region owing to the Brownian motion and in a case that a single particle crosses a light detection region by moving the position of the light detection region in a sample solution at a velocity quicker than the diffusional moving velocity of the single particle. FIG. 4C shows drawings explaining an example of the signal processing step of the detected signals in the procedure for detecting the existence of a single particle from the measured time series light intensity data (change in time of photon count) in accordance with the inverted scanning molecule counting method.

Figure 7A:
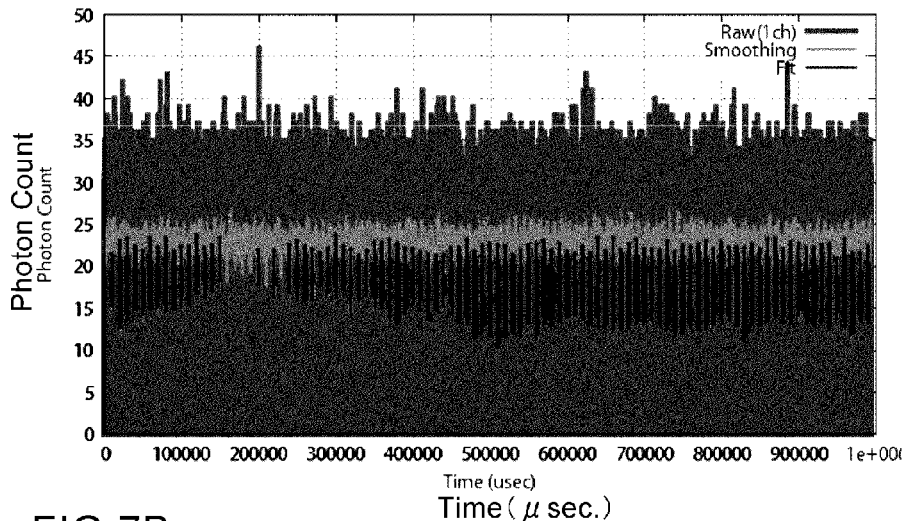
Figure 7B:
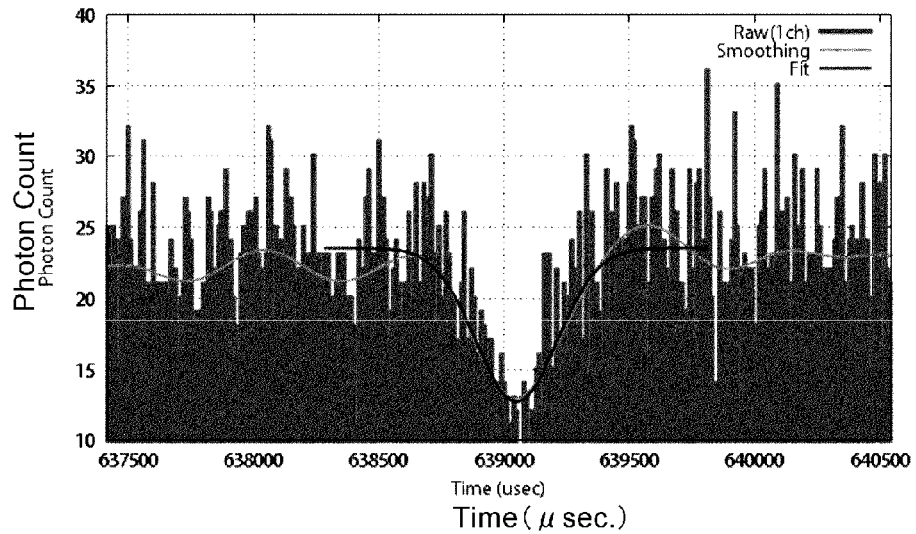
Figure 7C:
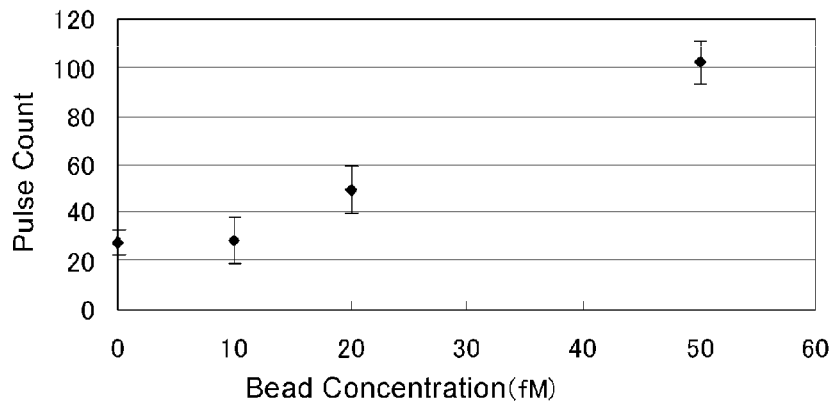

FIG. 7A is an example of time series light intensity data (photon count data) obtained in accordance with the inverted scanning molecule counting method using a solution where fluorescent dye was dissolved, containing magnetic beads at 10 mg/ml, and FIG. 7B is its enlarged view of a part in which a signal indicating the existence of a magnetic bead is observed. In the drawing, a curve obtained by smoothing data values and fitting curves to the signal of a magnetic bead are superimposed. FIG. 7C shows a relation between the magnetic bead concentrations in the solution and the numbers of signals indicating the existences of the magnetic beads detected in the time series light intensity data obtained in accordance with the inverted scanning molecule counting method.

EXPLANATIONS OF REFERENCE NUMERALS

1—Optical analysis device (confocal microscope)
2—Light source
3—Single mode optical fiber
4—Collimating lens
5—Dichroic mirror
6, 7, 11—Reflective mirror
8—Objective
9—Micro plate
10—Well (sample solution container)
12—Condenser lens
13—Pinhole
14a—Dichroic mirror or polarization beam splitter
14—Barrier filter
15—Multi-mode optical fiber
16—Photodetector
17—Mirror deflector
17a—Stage position changing apparatus
18—Computer

DESCRIPTION OF EMBODIMENTS

In the followings, preferable embodiments of the present invention are described in detail.

Structure of Single Particle Detection Device

Figure 1A:
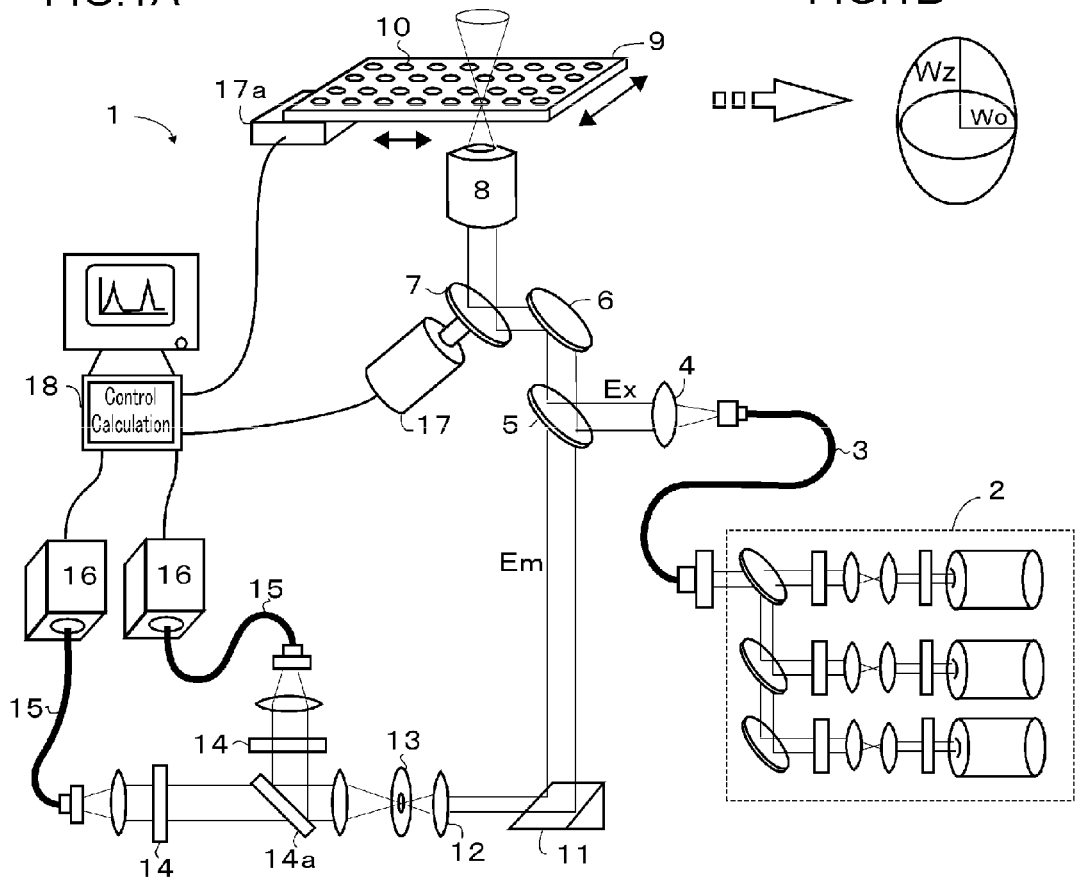

In the basic structure, a single particle detection device which realizes the single particle detection technique according to the present invention can be a device constructed by associating the optical system of a confocal microscope and a photodetector, enabling FCS, FIDA, etc., as schematically illustrated in FIG. 1A. Referring to this drawing, the single particle detection device 1 consists of an optical system 2-17 and a computer 18 for acquiring and analyzing data together with controlling the operation of each part in the optical system. The optical system of the single particle detection device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In this regard, in the sample solution, typically, single particles to be objects to be observed and arbitrary light-emitting substance which produces background light are dispersed or dissolved, and when no single particle has entered into the excitation region, the light-emitting substance is excited so that substantially constant light is emitted, becoming the background light; and when a single particle enters into the excitation region, the background light decreases.

Figure 1B:
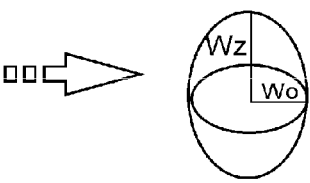

Then, the light (Em), emitted from the excitation region, passes through the objective 8 and the dichroic mirror 5, and the light is reflected on the mirror 11 and condensed by a condenser lens 12, and then the light passes through the pinhole 13 and transmits through the corresponding barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for the single particle detection are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian distribution having the peak at the center of the region. The effective volume is a volume of an approximate ellipsoid bordering a surface where the light intensity is reduced to $1/e^2$ of the peak intensity.), which is called as "confocal volume". Further, in the present invention, a light amount reduction because of the existence of a single particle in the background light which consists of faint light from several number of fluorescent dye molecules is detected, and thus, for the photodetector 16, preferably, a super high sensitive photodetector, usable for the photon counting, is used. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, in the presences of two or more specimens, quick measurements are achievable.

Figure 1C:
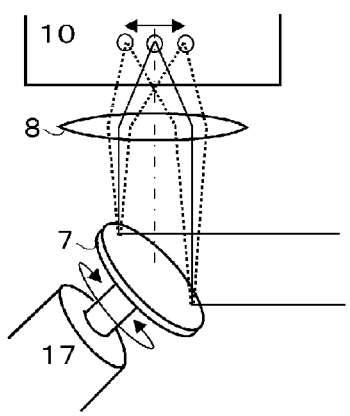
Figure 1D:
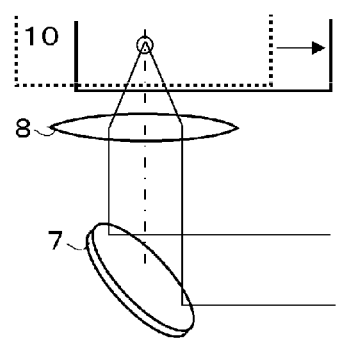

Furthermore, in the optical system of the above-mentioned single particle detection device, there is further provided a mechanism for scanning the inside of the sample solution with the light detection region, namely for moving the position of the focal region i.e. the light detection region, within the sample solution. For this mechanism for moving the position of the light detection region, for example, there may be employed a mirror deflector 17 which changes the direction of the reflective mirror 7, as schematically illustrated in FIG. 1C (the way of moving the absolute position of the light detection region). This mirror deflector 17 may be the same as that of a galvanomirror device equipped with a usual laser scan type microscope. Alternatively, as illustrated in FIG. 1D, the stage position changing apparatus 17a may be operated to move the horizontal position of the container 10 (micro plate 9) in which the sample solution is dispensed, thereby moving the relative position of the light detection region in a sample solution (the way of moving the absolute position of a sample solution.). Even in either of cases, in order to attain a desired moving pattern of the position of the light detection region, the mirror deflector 17 or stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). Moreover, by combining the way of moving the absolute position of the light detection region and the way of moving the absolute position of the sample solution, the absolute position of the light detection region may be moved together with moving the position of the sample solution. In this case, it is avoided that the same single particle is repetitively detected because of the light detection region passing through the same region in a short time. Or, by making the light detection region repetitively pass through the same region intentionally through the way of moving the absolute position of the light detection region so as to periodically detect the same single particle multiple times, the improvement in the accuracy of signals may be achieved. In this case, after performing the moving of the absolute position of the light detection region for a predetermined time, by moving the position of the sample solution intermittently and repetitively detecting the identical single particles in different places in the sample solution, the increase of the number of the single particles may be achieved. In this regard, although not illustrated, the position of the light detection region may be moved in the vertical direction by moving the objective 8 up and down, so that the track of the position of the light detection region is developed in three dimensions within the sample solution.

In the case that Light-emitting substance which generates background light emits light by multiple photon absorption, the above-mentioned optical system is used as a multiphoton microscope. In that case, since the light is emitted only from the focal region of the excitation light (light detection region), the pinhole 13 may be removed. When substance which generates background light emits light owing to a chemiluminescence or bioluminescence phenomenon without excitation light, the optical system 2-5 for generating excitation light may be omitted. When substance which generates background light emits light owing to phosphorescence or scattered light, the above-mentioned optical system of the confocal microscope is used as it is. Furthermore, in the device 1, as shown in the drawing, two or more excitation light sources 2 may be provided so that the wavelength of the excitation light can be appropriately selected in accordance with the wavelength of the light for exciting light-emitting substance. Similarly, two or more photodetectors 16 may also be provided so that separate detection can be performed depending upon the wavelengths. Moreover, background light may be provided by illumination light. In that case, the sample solution is illuminated with transmitted illumination (which may be Koehler illumination.) from above the objective. The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

The Principle of Single Particle Detection of the Present Invention As described in the column of "Summary of Invention", in the single particle detection technique of the present invention, briefly, the existence of a single particle is individually detected by the scanning molecule counting method of detecting the shadow of the single particle (hereafter, called the "inverted scanning molecule counting method"), namely, in the manner that the position of the light detection region is moved in the sample solution in the presence of background light and a reduction of the background light at the time of a single particle being encompassed by the light detection region is detected as a signal of the single particle, and thereby the count of the single particles or the information about their concentration in the sample solution is acquired. In the following, the principle of the inverted scanning molecule counting method according to the present invention will be explained.

1. Principle of Inverted Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement so that significant light intensity (photon count) can be always detected in the measuring term. When the concentration or number density of the light-emitting particle is lower than that, for example, at the level where the light-emitting particle rarely enters into the light detection region CV, no significant light intensity signal (photon count) would appear in a part of the measuring term, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA. In this scanning molecule counting method, briefly, a particle to be an observation object is a light-emitting particle dispersed in a sample solution, and, in the above-mentioned single particle detection device, measurement of light intensity is performed with moving the position of the light detection region. Then, when the light detection region encompasses a light-emitting particle, an increase of the observed value of light intensity arises because the light from the light-emitting particle reaches the light detector, and thus, the increase of the light intensity value will be detected and thereby the existence of one light-emitting particle will be detected individually. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution of a low particle concentration at the level where no sufficiently accurate analysis is available in FCS, FIDA, etc.

In the case of the usual "scanning molecule counting method" as described above, the particles to be observation objects are particles which emit light in a detected light wavelength band, and the particles which do not emit light in the detected light wavelength band cannot be detected. Thus, when a particle which does not emit light essentially is an observation object, it is required to attach a light emitting label, such as a fluorescent indicator, to the particle. However, depending on particles, it is possible that the attaching of a light emitting label is difficult, or the denaturation of the particle can occur due to the attaching of a light emitting label. Further, in the case of the way of identifying the light emitted by a particle as a signal indicating the existence of the particle, when an increase of the value on light intensity data arises due to stray light, scattered light or electric noise of a photodetector, it is possible that the increase of the value is erroneously identified as a signal of a light-emitting particle.

Thus, in the "inverted scanning molecule counting method" of the present invention, as noted above, the detection of a single particle is achieved by making background light emitted from the light detection region (or illuminating the light detection region with illumination light) and catching a reduction of the detected background light when a particle to be an observation object enter into the light detection region in the light measurement by the above-mentioned scanning molecule counting method. Concretely, similarly to the usual scanning molecule counting method, the light detection is performed with moving the position of the light detection region CV in the sample solution, namely, scanning the inside of the sample solution with the light detection region CV, by driving the mechanism for moving the position of the light detection region to change the optical path (the mirror deflector 17), or to move the horizontal position of the container 10 (micro plate 9) to which the sample solution has been dispensed, as schematically drawn in FIG. 2A. As noted, there is dispersed light-emitting substance in the sample solution so that a large amount of the light-emitting substance exists in the light detection region CV, and thus, basically, the light from those light-emitting substance is detected almost uniform during the moving of the light detection region CV (In the drawing, time to-t2). However, when the moving light detection region CV is passing through a region where one non light emitting light particle (or a particle having a low emitting light intensity in a detected light wavelength band) (t1), the volume of the region occupied by the light-emitting substance decreases so that the total amount of the light emitted by the light-emitting substance will decrease and a bell-shaped pulse form significant reduction of the light intensity (Em) will appear on the time series light intensity data as drawn on FIG. 2B. Thus, by conducting the moving of the position of the light detection region CV and light detection as described above and detecting one by one a significant pulse form reduction of the light intensity as illustrated in FIG. 2B, i.e., a signal indicating the existence of a single particle appearing during that time, the single particles are individually detected, and by counting their number, the information about the number, concentration or the number density of the single particle which exists in the measured region can be acquired.

The degree of the above-mentioned reduction of the light intensity can be estimated from the relation between the diameter of a single particle and the diameter of a light detection region. With reference to FIG. 2C, typically, the light intensity distribution in a light detection region has the maximum strength Imax at the center, and the distribution has the bell-shaped profile f(r) reducing in the direction of radius r as shown by the solid line in the drawing. Thus, using the radius a of the light detection region at which the f (r) becomes almost 0, the total amount α of the light emitted from the inside of the light detection region when no single particles to be observed exist in the light detection region is given by:

$$\alpha = 4\pi \int r^2 f(r) dr \text{ [Integration range is 0-}a\text{]}. \quad (1)$$

On the other hand, when a single particle having radius b enters into the light detection region and is located at the center of the light detection region as in the lower row of FIG. 2C, the light-emitting substance of the region will be eliminated, and thus, the light amount corresponding to the shaded region of the upper row of FIG. 2C will decrease. The light amount β corresponding to the eliminated light-emitting substance, i.e., a reduced amount is given by:

$$\beta = 4\pi \int r^2 f(r) dr \text{ [Integration range is 0-}b\text{]} \quad (2)$$

Thus, the ratio of reduction of light intensity can be estimated as β/α.

In this connection, when f (r) is a Gauss function and α=1 and a=1 are set, there is given:

$$f(r) = 0.684 \exp(-2r^2) \quad (3).$$

FIG. 2D is a graph of plotting the ratios of light intensity reduction β/α against to radius ratios b/a using Expression (3). With reference to the drawing, typically, when the ratio of background light variation is about 1% and the ratio of the light intensity reduction because of a single particle is 1% or less, no signals would become detectable, and thus, the ratio of the radius of a single particle to the radius of a light detection region, b/a, should be made 0.15 or more. Further, when the ratio of the light intensity reduction owing to a single particle is made not less than 10%, the ratio of the detectable single particle radius to the radius of the light detection region, b/a, becomes 0.35.

In this regard, in a case that a single particle to be observed is a quencher or an acceptor in fluorescence energy transfer, since the single particle absorbs the surrounding light (for example, 10 nm), the detectable single particle radius can be smaller than the radius as illustrated above. Moreover, the radius as illustrated above is a value in case that a single particle to be observation object does not emit light substantially in a detected light wavelength band, and thus, when a single particle emits the light at a certain degree in a detected light wavelength band, the detectable single particle radius can be larger than the illustrated radius.

Operation Processes of Scanning Molecule Counting Method

Figure 3:
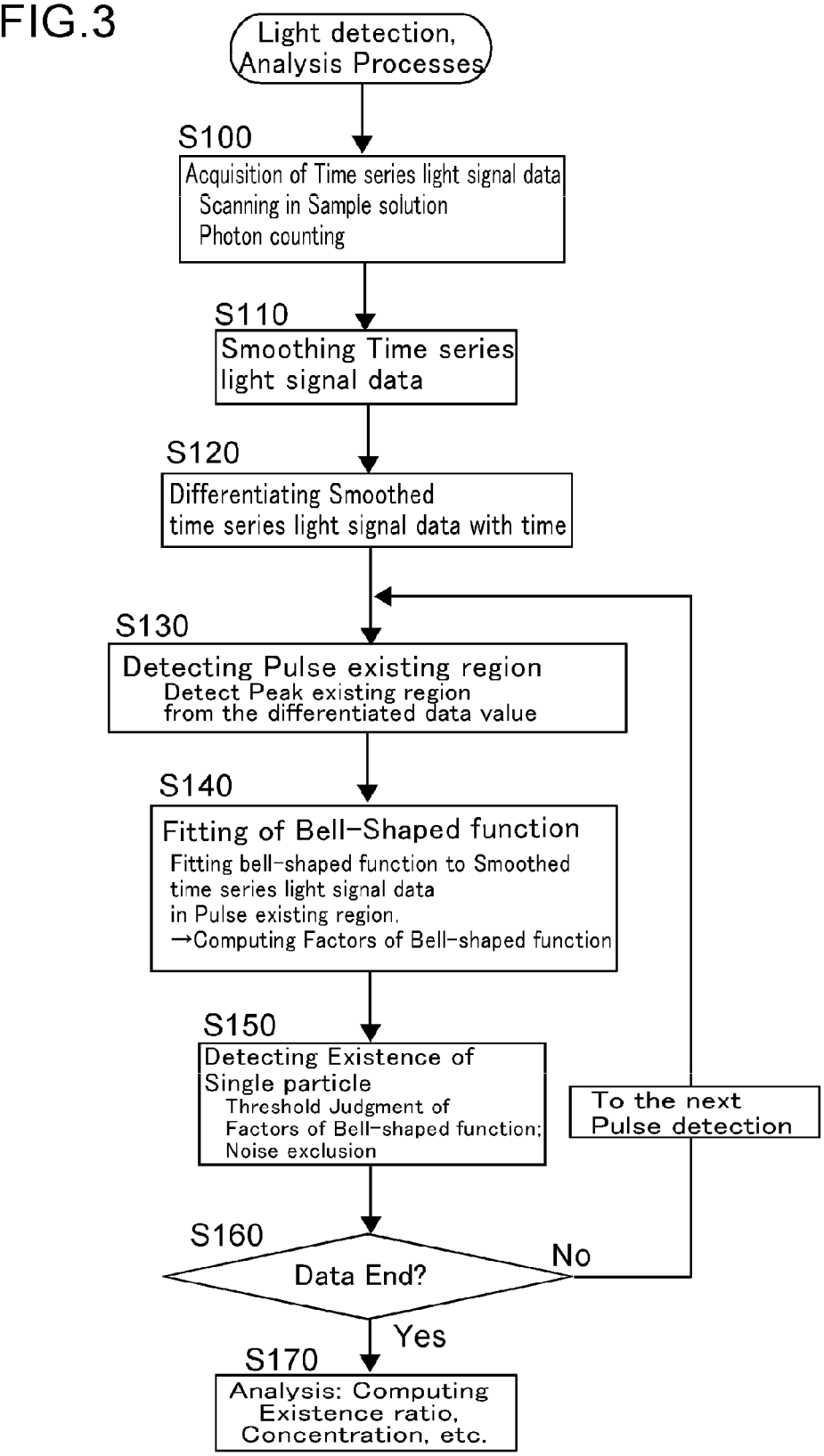

In the embodiment of the inverted scanning molecule counting method in accordance with the present invention with the single particle detection device 1 as illustrated in FIG. 1A, concretely, there are conducted (1) the preparation of a sample solution containing single particles and light-emitting substance generating background light; (2) the process of measuring the light intensity of the sample solution and (3) the process of analyzing measured light intensities. FIG. 3 shows the processes in this embodiment in form of the flow chart.

(1) Preparation of a Sample Solution

The particle to be an object to be observed in the inventive single particle detection technique may be an arbitrary particle as long as it is dispersed in a sample solution and moving at random in the solution and has a particle diameter of preferably not less than 15% and more preferably not less than 35% of the diameter of the light detection region; and the particle may be, for instance, a biological molecule, i.e. a protein, a peptide, a nucleic acid, a lipid, a sugar chain, an amino acid, etc. or an aggregate thereof, a virus, a cell, a non-biological particle (for example, an atom, a molecule, a micelle, a liposome, a metallic colloid, a bead (a magnetic bead, a polystyrene bead, a latex bead, etc.), a quencher (azobenzenes (dabcyl, BHQ, etc.), a metallic particle, etc.)

In this respect, as already described in the column of "Summary of Invention", in the present invention, a significant reduction of the light amount from the light detection region owing to a single particle existing in the light detection region is detected, and thus, the single particle may be a particle whose emitting light intensity is lower than the background light in the detected light wavelength band. As for the light-emitting substance giving background light, an arbitrary light-emitting molecule, for example, a fluorescent molecule, a phosphorescent molecule, and a chemi- or a bioluminescent molecule may be used, and the light-emitting substance is dissolved or dispersed in a sample solution at a concentration which makes several molecules to always exist in the light detection region. The sample solution is typically an aqueous solution, but not limited to this, and it may be an organic solvent or other arbitrary liquids.

(2) Measurement of Light Intensity of Sample Solution (FIG. 3—step 100)

The light intensity measurement in the optical analysis by the inverted scanning molecule counting method of the present embodiment may be performed in a manner similar to the measuring process of light intensity in FCS or FIDA except that the moving of the position of the light detection region in a sample solution (scanning in a sample solution) is conducted by driving the mirror deflector 17 or stage position changing apparatus 17a during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or stage position changing apparatus 17a, drives the mirror 7 (galvanomirror) or the micro plate 9 on the stage of the microscope to move the position of the light detection region in the well 10, and simultaneously with this, the photodetector 16 sequentially converts the detected light into electric signals and transmits it to the computer 18, which generates the time series light intensity data from the transmitted signals and stores it in an arbitrary manner. In this regard, the photodetector 16 is typically a super high sensitive photodetector which can detect the presence or absence of an arrival of a single photon, and thus, when the light detection is conducted by the photon counting, the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected single particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a single particle to be observed from the measured time series light intensity data or the counting of the number of single particles, it is preferable that the moving speed is set to a value quicker than the moving speed in the random motion, i.e., the Brownian motion of a single particle. Since the particle to be observed in the inventive single particle detection technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random (as noted, the excitation light intensity in the light detection region is reduced from the peak at the center of the region toward its outside.), so that it becomes difficult to determine a significant light intensity change corresponding to each single particle. Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the most upper row of FIG. 4C (When a single particle passes through the light detection region in an approximately straight line, the profile of the light intensity change is similar to the inverted form of the excitation light intensity distribution.) and the correspondence between each particle and light intensity can be easily determined.

Concretely, the time $\Delta t$ required for a particle having a diffusion coefficient D to pass through the light detection region of radius Wo (confocal volume) by the Brownian motion is given from the Expression of the relation of mean-square displacement:

$$(2Wo)^2 = 6D \cdot \Delta t \qquad (4)$$

as:

$$\Delta t = (2Wo)^2/6D \qquad (5),$$

and thus, the velocity of the particle moving by the Brownian motion (diffusional moving velocity) Vdif, becomes approximately $$V\text{dif} = 2\ Wo/\Delta t = 3D/Wo \qquad (6)$$

Then, with reference to this, the moving speed of the position of the light detection region may be set to a value sufficiently quicker than Vdif. For example, when the diffusion coefficient of a particle to be observed is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, such as 15 mm/s. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data in the sample solution is obtained by the above-mentioned processes, there are performed detection of a signal of a single particle, counting of single particles, and various analyses, such as concentration calculation, etc. in the computer 18 through processes in accordance with programs memorized in a storage device.

(i) Individual Detection of a Signal of a Single Particle

When the track of one particle in its passing through the light detection region is approximately straight as shown in FIG. 4B, the light intensity variation in the signal corresponding to the particle in the time series light intensity data has a downwardly convex, almost bell shaped profile reflecting the light intensity distribution in the light detection region (determined by the optical system) (see the most upper row of FIG. 4C). Thus, basically in the scanning molecule counting method, when the time width of a reduction of the light intensity descending below an appropriately set threshold value measured from the background light continues is in a predetermined range, the signal having the profile of the light intensity reduction may be judged to correspond to one particle having passed through the light detection region, and thereby one particle is detected. And a signal, whose time width for which light intensity reduction descending below the threshold value continues is not in the predetermined range, is judged as noise or a signal of a contaminant. Further, when the light intensity distribution in the light detection region can be assumed as a Gaussian distribution, downwardly convex from the background light Ibg:

$$I=Ibg-A\cdot\exp(-2t^2/a^2) \qquad (7),$$

and when the intensity A and the width a, computed by fitting Expression (7) to the profile of a significant light intensity reduction (a profile which can be clearly judged not to be a fluctuation of the background light), are within the respective predetermined ranges, the profile of the light intensity may be judged to correspond to one particle having passed through the light detection region, and thereby the detection of one particle will be done (The signal with the intensity A and the width a out of the predetermined ranges may be judged as a noise or a contaminant signal and ignored in the later analysis, etc.).

As an example of processing methods of performing collective detections of single particles from time series light intensity data, first, a smoothing treatment is performed to the time series light intensity data (FIG. 4C, the most upper row "detected result (unprocessed)") (FIG. 3—step 110, FIG. 4C mid-upper row "smoothing"). The light emission by light-emitting substance is stochastic and the light intensity is comparatively weak so that small increase and decrease of the light intensity will occur, and such small increases and decreases (fluctuation) in the light intensity would deteriorate the detection accuracy of a signal indicating the existence of a single particle. The smoothing makes it possible to disregard such small increases and decreases on the data. The smoothing treatment may be done, for example, by the moving average method, etc. In this regard, parameters in performing the smoothing treatment, e.g., the number of datum points in one time of the averaging, the number of times of the moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differential values with time of the time series light intensity data after the smoothing treatment is computed (step 120). As illustrated in FIG. 4C, the mid-low row "time differential", in the time differential values of time series light signal data, the variation of the values increases at the time of the signal value change, and thereby, the start point and the end point of a significant signal can be determined advantageously by referring to the time differential value.

After that, a significant pulse signal is detected sequentially on the time series light intensity data, and it is judged whether or not the detected signal is a signal corresponding to a single particle. Concretely, first, on the time series time-differential value data of the time series light intensity data, the start point and the end point of one pulse signal are searched and determined by referring to the time differential values sequentially, so that a pulse existing region will be specified (step 130). When one pulse existing region has been specified, the fitting of a downwardly convex, bell-shaped function is applied to the smoothed time series light intensity data in the pulse existing region (FIG. 4C, the lower row "bell-shaped function fitting"), and then, parameters of the pulse of the bell-shaped function, such as the peak intensity (Maximum reduction amount from the background light), Ipeak; the pulse width (full width at half maximum), Wpeak; the correlation coefficient in the fitting (of the least square method), etc. are computed (step 140). In this regard, although the bell-shaped function to be used in the fitting is typically Gauss function, it may be Lorentz type function. Then, it is judged whether or not the computed parameters of the bell shaped function are within the ranges assumed for the parameters of the bell-shaped profile drawn by a pulse signal detected when one particle passes the light detection region, namely, whether or not the peak intensity, pulse width and the correlation coefficient of the pulse are in the predetermined ranges, respectively, for instance, whether or not the following conditions:

20 μsec.<pulse width<400 μsec.

Peak intensity>4.0[pc/10 μsec.]

Correlation coefficient>0.95 (A)

are satisfied, etc. (step 150) Then, a signal whose computed parameters of the bell shaped function are within the ranges assumed for a signal corresponding to one signal is judged as a signal corresponding to one particle. On the other hand, a pulse signal whose computed parameters of the bell type function are not within the assumed ranges is disregarded as noise.

The searching and judgment of a pulse signal in the above-mentioned processes of steps 130-150 may be repetitively performed over the whole region of time series light intensity data (Step 160). In this connection, the processes for detecting individually a signal of a single particle from the time series light intensity data may be performed by an arbitrary way, other than the above-mentioned procedures.

(ii) Determination of a Particle Concentration

Furthermore, by counting the number of signals of detected single particles, the determination of the number of particles may be done (counting of particles). Also, when the volume of the whole region which the light detection region has passed through is computed in an arbitrary way, the number density or concentration of a single particle in the sample solution can be determined from its volume value and the number of particles (Step 170).

Although the whole volume of the region which the light detection region has passed through may be theoretically computed based upon the excitation light or detected light wavelength the numerical aperture of lenses, the adjustment conditions of the optical system, it may be experimentally determined, for instance, from the number of particles, which have been detected by conducting, with a solution having a known light-emitting particle concentration (reference solution) under the same condition as that for the measurement of a sample solution to be tested, the light intensity measurement, the detection of particles and the counting thereof, and the concentration of the particle in the reference solution. Concretely, for example, supposing the number of detected single particles is N in a reference solution of the particle concentration (number density) C, the whole volume Vt of the region the light detection region has passed through is given by:

$$Vt=N/C \qquad (8).$$

Alternatively, the plurality of solutions of different single particle concentrations are prepared as reference solutions and the measurement is performed for each of the solutions, and then, the average value of the computed Vt is determined as the whole volume Vt of the region which the light detection region has passed through. Thus, when Vt is given, the particle concentration c of the sample solution, whose counting result of the single particles is n, is given by:

$$c=n/Vt \qquad (9)$$

In this regard, the volume of the light detection region and the volume of the whole region which the light detection region has passed through may be given by an arbitrary method, for instance, using FCS and FIDA, instead of the above-mentioned method. Further, in the device of this embodiment, there may be previously memorized in a storage apparatus of the computer 18 the information on the relations (Expression (8)) between concentrations C and particle numbers N of various standard particles for assumed moving patterns of the light detection region, so that a user of the device can appropriately use the memorized information on the relation in conducting an optical analysis.

Accordingly, in the inverted scanning molecule counting method in which a sample solution is scanned with the light detection region and particles are detected individually, the counting of particles in the sample solution, the determination of concentration, etc. can be achieved according to the above-mentioned procedures (4) Single Particle Detection Process of Detecting a Fixed Number of Signals In the above-mentioned single particle detection process, after performing light measurement for a certain set time, signals of single particles are detected on the obtained light intensity data. In that case, when the particle concentration in a sample solution is unknown, the light intensity is measured for a certain fixed measuring time and the measuring time will be set long enough for the sake of a low particle concentration. On the other hand, when the particle concentration in a sample solution is high, the light intensity measurement will be continued more than a time necessary to determine a characteristic, such as a concentration, at the allowable or satisfactory accuracy. Moreover, in a case that the particle concentration in a sample solution is lower than a concentration which the experimenter has assumed and the set measuring time is insufficient, the error of the result would become large. Then, for another manner of the single particle detection process, the light intensity measurement with moving a light detection region and the detection of a signal of a single particle may be repeated until the number of signals reaches a predetermined number; the time taken for the number of signals to reach the predetermined number may be measured; and the particle concentration may be determined based on the time taken for the number of the signals of the single particles to reach the predetermined number. According to this structure, for a sample solution of a high particle concentration, the time taken for the light intensity measurement can be shortened, while for a sample solution of a low particle concentration, it becomes possible to continue the light intensity measurement until the particle count which attains the accuracy required for a result (namely, particle concentration) is obtained. And, by setting the predetermined number to be reached by the number of signals of single particles to the particle count which achieves the accuracy required for a result, the particle count which achieves the accuracy required for the result will be reflected in the time taken for the number of signals of single particles to reach the predetermined number, and thus, it is expected that the concentration value of the particles determined based on that time has the allowable or satisfactory accuracy.

(i) Basic Principle

A particle concentration value and a time taken for the number of signals to reach a predetermined number are associated with as follows: In a case that a light detection region is moved at a scanning speed u for time τ in a sample solution having a certain particle concentration C, assuming that the cross sectional area of the light detection region is S, the number X of detected signals is:

$$X = CSu\tau N_A \quad (10)$$

where $N_A$ is the Avogadro's number. Thus, supposing it takes a time T for the number of the signals to reach the predetermined number XE, the light-emitting particle concentration C is given as a function of the time T by:

$$C = XE/(STuN_A) \quad (11)$$

In this regard, in Expression (11), based on the time T, taken for the number of the signals to reach the predetermined number XE, and the number XE of the detected particles, a detection rate V of the particles per unit time is given by:

$$V = XE/T \quad (12),$$

and therefore, the particle concentration C is represented by:

$$C = V/(SuN_A) \quad (13)$$

In this Expression (13), the particle concentration C is proportional to the detection rate V in the first-order so that the correspondence relation between the particle concentration C and the detection rate V is intelligible, and therefore, in an actual experiment, the particle concentration C may be determined using the detection rate V.

(ii) Processing Operation Procedure

Figure 5:
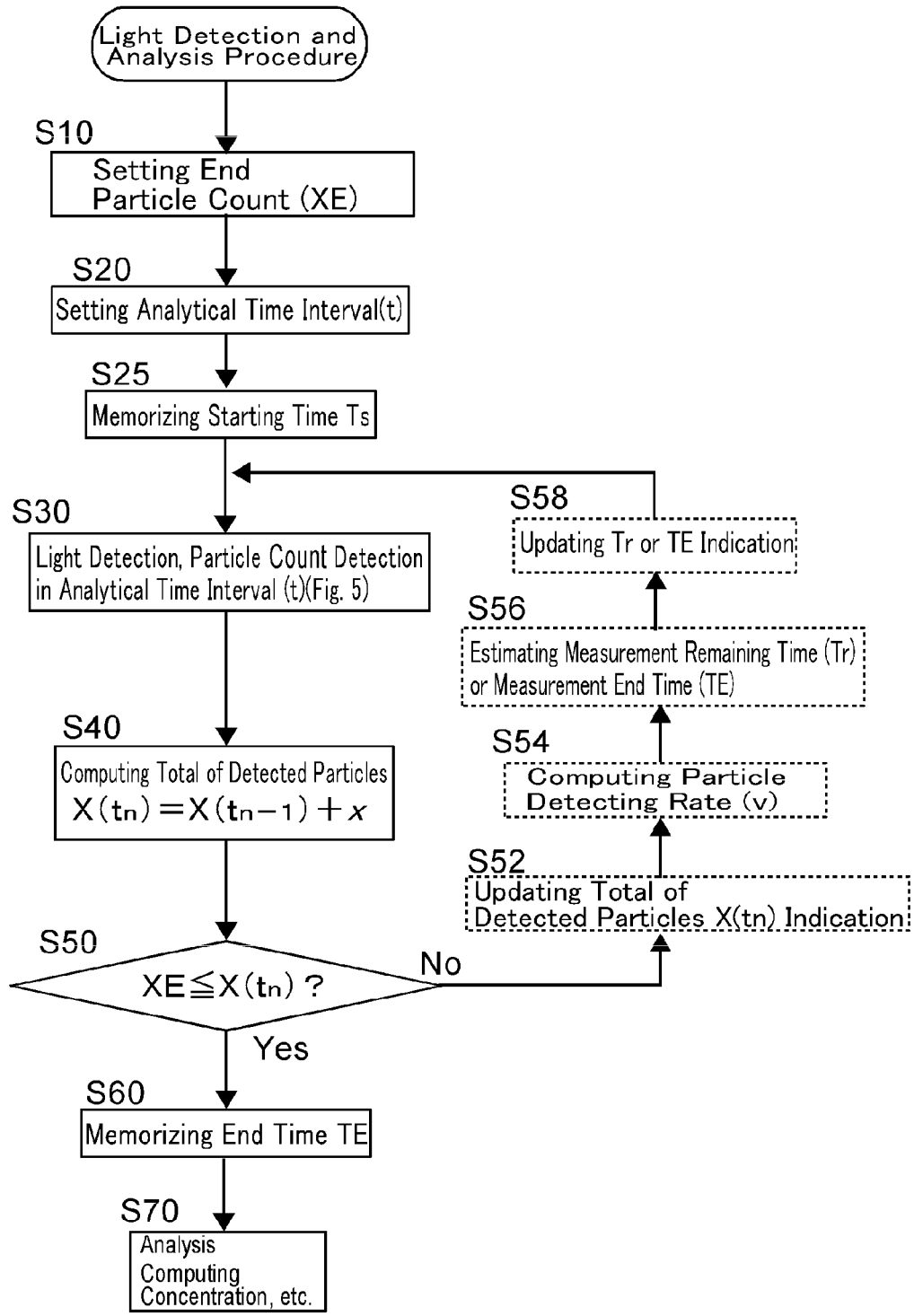
FIG. 5 is a diagram showing another manner of the procedures of the inverted scanning molecule counting method performed according to the present invention in the form of a flow chart.

The single particle detection process for detecting a fixed number of signals may be performed, for example, by the procedures shown in the flow chart of FIG. 5. In the example of this drawing, briefly, a series of processes: the moving of the position of a light detection region, the detection of the light from the light detection region, the detection of signals of single particles and the counting of the detected particle signals are repetitively performed in every analytical time interval t (a predetermined time interval) until the detected particle count X reaches the end particle count XE (a predetermined number to which the number of single particle should reach). In this regard, it should be understood that a series of processes and structures described below are realized by the processing operations of the computer 18.

(a) Initial Setting

Referring to FIG. 5, in the operation processes, concretely, first, after dispensing a sample solution into the well(s) 10 of the micro plate 9 and putting it on the stage of the microscope, when a user inputs to the computer 18 a command of staring processes of a light intensity measurement and detecting and counting particles, the computer 18 performs, as the initial setting, the setting of the end particle count XE (step 10) and the setting of the analytical time interval t (step 20). The end particle count XE and the analytical time interval t may be arbitrarily set by the user. In order to achieve an accuracy requested in a result value of a particle concentration, the end particle count XE can be appropriately determined with reference to a result of a preliminary experiment using a solution having a known particle concentration. For the analytical time interval t, an arbitrary time interval enough shorter than the period until the number of particles (X) reaches the end particle count (XE) after starting the process may be appropriately set, considering the processing speed, etc. in the device 1. Further, for each of the end particle count XE and analytical time interval t, a value, determined beforehand with reference to a result of a preliminary experiment using a solution having a known particle concentration, may be memorized in the device 1 so that the memorized value can be used automatically or by a user's choice.

(b) Detection of the Number of Particles

When the setting of the end particle count XE and analytical time interval t has been made, the light intensity measuring process, the detection of signals of particles from measured light intensity data and detection of the number of particles x (step 30) in the analytical time interval t according to the scanning molecule counting method; and a process of accumulating the number of the particles x detected in step 30 and computing the total number X(tn) of the particles (step 40) are repetitively performed every analytical time interval t until the total number X(tn) of the particles reaches the end particle count XE (step 50) as described below. In this regard, prior to the repetitive execution of processes of steps 30-50, the starting time Ts of a series of processes may be memorized (step 25).

The process of the light detection and particle count detection in step 30 may be the same as in the process shown in FIG. 3. Briefly, the light intensity measurement is conducted for the analytical time interval t with moving the position of the light detection region within the sample solution (scanning the inside of the sample solution), and then, in the time series light intensity data obtained in the analytical time interval t, the detection of a signal indicating the existence of a single particle and the counting of the detected number are performed in the computer 18 by the processes according to programs memorized in a storage device.

Thus, when the number of particles x in the time series light intensity data in the analytical time interval t is detected, the total number $X(t_n)$ of the detected particles is computed with $$X(t_n)=X(t_{n-1})+x \qquad (14)$$

(FIG. 5—step 40). Here, $X(t_{n-1})$ is the total number of the particles detected till the last analytical time interval t, and its initial value is 0. And, steps 30-40 are repeated every analytical time interval t until the total number of the detected particles X(tn) reaches the end particle count XE, namely, $$X(t_n) \geq XE \qquad (15)$$

is established (step 50). Then, during the repeating of steps 30-50, when Expression (15) is established, the processes of the light intensity measurement of the sample solution and the detecting and counting of the particles are ended. When the repetitive operations of steps 30-50 are completed, the end time TE may be memorized (step 60).

(c) Indication of the Number of Particle and the Measurement End Time

By the way, in the period of the repetitive execution of steps 30-50 in every analytical time interval t (until Expression (15) is established), the total number of the detected particles $X(t_n)$ and/or the measurement end time TE or the measurement remaining time Tr may be indicated on a display, such as a monitor, etc. of the computer 18. According to this structure, it is advantageous in that a user can predict when an executed measurement is ended by seeing those indications.

For carrying out an indication as described above, when Expression (15) is not established in the judgment of step 50 of FIG. 5, the respective processes shown in dotted line in the drawing are executed. Concretely, first, the newest total number of the detected particle X(tn) computed in step 40 is indicated on the display (step 52). In this connection, when the repetitive executions of steps 30-50 have been already executed, the value of the total number X(tn) of the detected particles so far is updated. Subsequently, in order to compute the measurement end time TE or the measurement remaining time Tr, the detection rate v of the particle after the start of the processes of step 30-50 is computed (step 54). The detection rate v of the particle till the present may be given by:

$$v=X(t_n)/(Tp-Ts) \qquad (16)$$

Here, Tp is the present time. Thus, using the detection rate v of the particle, the measurement remaining time Tr (time to the end of the processes of steps 30-50) is estimated as:

$$Tr=(XE-X(t_n))/v \qquad (17)$$

Moreover, the measurement end time TE (time of the end of the processes of steps 30-50) is estimated as:

$$TE=Tp+Tr \qquad (18)$$

(Step 56). Then, the estimated measurement end time TE or the measurement remaining time Tr is indicated on the display (step 58). In this connection, when the repetitive executions of steps 30-50 have been already executed, the already indicated values are updated. Further, when $X(t_n)=0$, it may be indicated that Tr and TE are unknown without calculating Expression (17) or (18).

By the way, as already noted, the above-mentioned processes of steps 30-50 in FIG. 5 are repeated every analytical time interval t. In this respect, the light intensity measurement of step 100 of FIG. 3 may be continuously performed from the start of measurement to its end even during the execution of the signal processing steps other than step 100. Namely, in the processes of the light detection and particle count detection, when the light intensity measurement for the analytical time interval t of one cycle is completed, the light intensity measurement in the analytical time interval t of the following cycle is performed continuously, and simultaneously, the processes of the detecting and counting of signals of particles from the light intensity data acquired in the analytical time interval t of the completed cycle are performed in the computer 18. Thereby, the detecting and counting of particles will be achieved in real time.

(3) Analysis, Such as Concentration Computation, Etc.

Then, when the number of particles reaches the end particle count, an analysis, such as a concentration computation, etc., may be performed using the time T (=TE−Ts) until the number of particles reaches the end particle count or other information which can be obtained from the detected signal(s) of the light-emitting particle(s) (step 70). As already noted, for a particle concentration, a particle detection rate V is computed with Expression (12) from the time T to reach the end particle count and the end particle count XE, and the particle concentration is determined from the particle detection rate V, using the relation of Expression (13).

In this regard, although the cross sectional area S of the passing region of the light detection region in Expression (10)-(13) may be computed theoretically based on the wavelength of excitation light or detected light, the numerical aperture of a lens and the adjustment condition of the optical system, the cross sectional area S may be determined experimentally, for example, from the number of particles, detected by performing the light intensity measurement, the detecting and counting of particles as explained above for a solution having a known particle concentration (a control solution) under the same conditions as the measurement of a sample solution to be tested, and the particle concentration of the control solution. Concretely, for example, for a control solution having a particle concentration C, supposing the number of detected particles in a light intensity measurement performed at the moving speed uo for a certain time τo is N, the cross sectional area S of the passing region of the light detection region is given by:

$$S=N/(C \cdot N_A \cdot uo \cdot \tau o) \qquad (19)$$

Furthermore, by preparing the plurality of solutions of different particle concentrations as control solutions and performing measurements for the respective solutions, the average of computed Ss may be employed as the cross sectional area S of the light detection region.

Figure 6A:
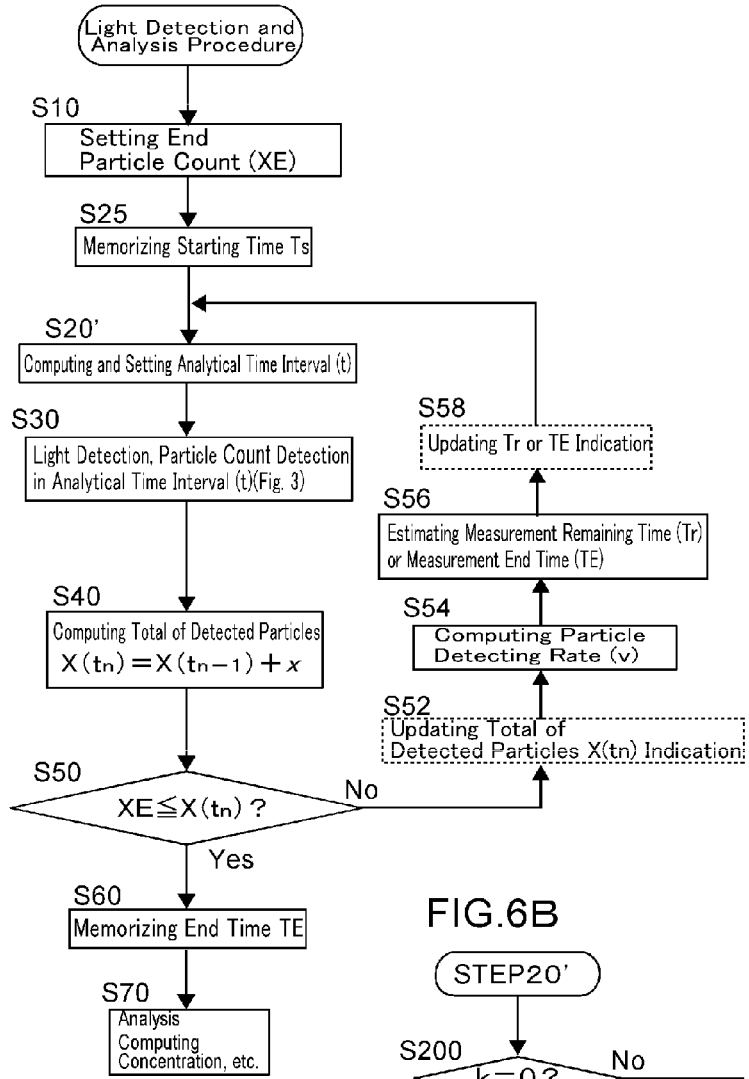
FIGS. 6A and 6B is a diagram showing the yet other manner of the procedures of the inverted scanning molecule counting method performed according to the present invention in the form of a flow chart.
Figure 6B:
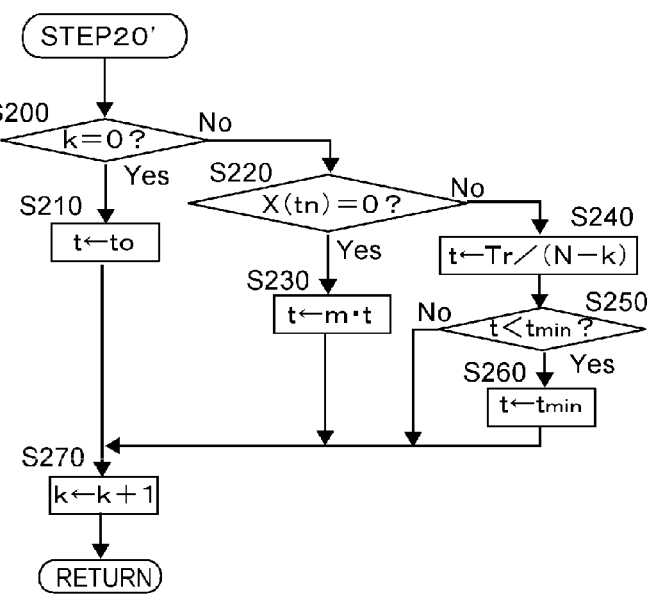

(e) Modified Examples of Processes of Light Intensity Measurement of a Sample solution and Detecting and Counting of Particles In the above-mentioned processes of the light intensity measurement of a sample solution, and the detecting and counting of particles, as an alternative manner, the analytical time interval t may not be a fixed value but may be modified according to the detecting condition of the particles. FIG. 6A shows in the form of a flow chart the processes of the light intensity measurement of a sample solution and the detecting and counting of particles, designed so as to include a process (step 20') of modifying the analytical time interval t according to the condition of detecting particles, and FIG. 6B shows the process of calculating the analytical time interval t in step 20' in the form of a flow chart. In this regard, in FIG. 6A, the same processes as in FIG. 5 are provided with the same step numbers.

Referring to the drawing, in the processes of FIG. 6A, 6B, whenever the light intensity measurement for the analytical time interval t is completed, the analytical time interval t is modified (step 20'). Further, especially the processes in the illustrated example are designed to execute the processing cycles of the light intensity measurement and the detecting and counting of particles only a predetermined number of times N (referred to as "number of times of scheduled updating" in the following.) in one measurement from its start until the number of particles reaches the end particle count XE. Concretely, first, when the processes of the light intensity measurement, the detecting and counting of particles are performed in the beginning after the setting of the end particle count XE (step 10) and the memorizing of the start time Ts (step 25) for the initial setting, namely, when the execution times k of the processing cycle of the light intensity measurement and the detecting and counting of particles is 0, the initial value to, arbitrarily settable, is given as the analytical time interval t (see FIG. 6B steps 200, 210). And, the execution times k of the processing cycle increases by one (step 270), and the processes of the light intensity measurement and the detecting and counting of particles for the analytical time interval t are performed (steps 30-50) similarly to the processes described in FIG. 5. Then, when the number of particles x of the first cycle (=X ($t_1$)) is obtained, the particle detection rate v (step 54) and the measurement remaining time Tr (step 56) are computed sequentially. In this connection, similarly to the case of FIG. 5, the total number of the detected particles X ($t_n$) and/or the measurement end time TE or the measurement remaining time Tr are indicated on a display, such as a monitor, etc. of the computer 18 (steps 52 and 58). Also, when the number of particles has reached the end particle count XE in the first processing cycle, the processes of the light intensity measurement and the detecting and counting of particles are ended (step 50).

After the first processing cycle, the modifying of the analytical time interval t and the processing cycle of the light intensity measurement and the detecting and counting of particles, similar to those in FIG. 5, (Steps 20', 30-58) are repeated until the number of particles reaches the end particle count XE. In that case, in step 20' of modifying the analytical time interval t, first, it is judged whether or not the number of particle X(tn) detected so far is 0 (step 220). If X(tn)=0, the analytical time interval t in the last cycle may be increased m times (m is one or more positive value). If X(tn)>0, using the measurement remaining time Tr, the number of times of scheduled updating N, and the execution time k of the processing cycle, the analytical time interval t is computed by:

$$t=Tr/(N-k) \quad (20)$$

(step 240). In this connection, for the analytical time interval t to be computed, its lower limit may be set, and when the analytical time interval t is less than the lower limit tmin, the analytical time interval t may be set to the lower limit tmin (steps 250, 260). As described above, according to the manner in which the analytical time interval t is modified, the condition of detecting the particles to be observation objects in the sample solution is reflected in the measurement remaining time Tr, and therefore, the analytical time interval t will be optimized according to the condition of detecting particles.

In order to verify the validity of the present invention explained above, the experiments described below were conducted. In this regard, it should be understood that the following embodiments illustrate the validity of the present invention only, not intended to limit the scope of the present invention.

Embodiment 1

It has been verified that, in the time series light intensity data obtained in the light measurement according to the inverted scanning molecule counting method, the signal indicating the existence of a single particle is detectable and the particle concentration is detectable.

Sample solutions were prepared by dissolving, in a solution of 10 mM Tris-HCl (pH 7.0), fluorescent dye, ATTO488 (ATTO-TEC) as light-emitting substance for generating background light at 12.5 µM or 15 nM and further dispersing magnetic beads of diameter of 1 µm (Dynabeads(registered trademark) MyOne Streptavidin C1:invitorgen) as single particles to be observed at various concentrations (the magnetic beads employed here are particles which do not emit light substantially.). In the light measurement, a single molecule fluorescence measuring apparatus MF20 (Olympus Corporation), equipped with the optical system of a confocal fluorescence microscope and a photon counting system, was used, and time series light intensity data (photon count data) were acquired for each of the above-mentioned sample solutions containing the fluorescent dye and magnetic beads in accordance with the manner explained in the above-mentioned "(2) Measurement of Light Intensity of a Sample Solution". Further, the diameter of the confocal volume (light detection region) is adjusted to 1 µm, and the moving speed of the position of the light detection region in the sample solution was set 15 mm/second, BIN TIME was set to 10 µseconds and measurements for 100 seconds were performed.

In the data processing after the above-mentioned light measurement, individual detection of the signal of a single particle and counting of the number of signal were performed in time series photon count data. In the detection of the signal of a single particle, in accordance with the manner described in "(i) Individual Detection of a Signal of a Single Particle" and steps 110-160 of FIG. 3, the smoothing treatment was performed to the time series photon count data, and after determining the start point and the end point of a pulse signal in the smoothed data, the fitting of the downwardly convex Gauss function (Expression (7)) was carried out to each pulse signal by the least-squares method, and thus, the peak intensity (the reduction amount of light intensity), pulse width (full width at half maximum), and correlation coefficient (in the Gauss function) were determined. Then, only the pulse signals satisfying the following conditions:

20 µsec.<pulse width<400 µsec.

Peak intensity>4[pc/10 µsec.]

Correlation coefficient>0.95     (A)

were extracted as signals of single particles, and the number of the signals was counted.

FIG. 7A shows a part of the time series photon count data (Raw) obtained using a 10 µW laser light of 488 nm as excitation light for the solution of the fluorescent dye concentration at 12.5 µM in which the magnetic beads were dispersed at 5 pM (5 mg/(ml)) as the sample solution. Here, the detected light was detected with a band pass filter whose transmitting wavelength was 650-690 nm and a band pass filter whose transmitting wavelength was 660-710 nm. In this drawing, the smoothed data (Smoothing) and fitting curves (Fitting) are also shown. Further, FIG. 7B is an enlarged view of the time series photon count data shown in FIG. 7A. As understood clearly with reference to these drawings, especially FIG. 7B, there was observed a light intensity reduction which could be fit with a downwardly convex bell shaped function in the time series photon count data. The ratio of the intensity of the signal of a bead to the background light intensity was −61% in the largest one and −16% in the smallest one. (The ratio of the intensity of the signal of a bead to the background light intensity was the value obtained by dividing the integrated intensity of the pulse signal acquired by integrating the differences between the fluorescence intensities and the background in the duration of 200 μsec. before and after the pulse signal with the integration value of the Gauss function whose height was the average of the background light intensity and whose full width at half maximum was 100 μsec. Although the lower limit of such a peak minimum value is decided depending on the accuracy of a peak detection algorithm or the stability of background, the upper limit of the peak maximum does not exist.)

FIG. 7C is a drawing of plotting against magnetic bead concentrations the numbers of signals obtained from time series photon count data acquired using a 50-μW laser light of 488-nm as the excitation light for the sample solutions in which the magnetic beads were dispersed at 0 fM, 10 fM, 20 fM, and 50 fM, respectively, in the solution of fluorescent dye concentration at 15 nM. In this regard, the detected light was detected with a band pass filter whose transmitting wavelength was 510-560 nm. Further, in the light measurement, the sample container was moved at 1 mm/sec. along a circular track of diameter of 1 mm as well as the moving of the light detection region (at 15 mm/sec.) by changing the optical path. Then, the signals having the S/N ratio of 0.35 or more were counted as particle signals among the pulse form signals which could be approximated with the Gauss function. As understood from FIG. 7C, the numbers of detection signals were almost proportional to the magnetic bead concentrations in the case of the magnetic bead concentrations of 10 fM or more.

From the above results, it has been shown that the light intensity reduction to which a downwardly convex bell shaped function can be fit is a signal indicating the existence of a single particle (magnetic bead) in the time series photon count data observed in FIG. 7B and the particle concentration in a sample solution can be determined by counting the light intensity reductions.

Thus, as understood from the results of the above-mentioned embodiments, according to the inverted scanning molecule counting method taught by the present invention, the detection of a non-light-emitting single particle dispersed in a sample solution and the acquisition of the information on its concentration become possible. Especially, since in the present invention the signal of a single particle is detected individually, detection of a particle is possible even when the particle concentration in a sample solution is lower than the concentration range requested in optical analysis techniques, such as FCS, and this feature will be advantageous in conducting analysis of a rare or expensive sample often used in the field of medical or biological research and development. Moreover, in the case of the present invention, the particle to be observed is not a light-emitting particle, and therefore, since the attaching of a light emitting label is unnecessary, any artifact due to the attaching of a light emitting label is avoided.

The invention claimed is:

1. A single particle detection device which detects a single particle dispersed and moving at random in a sample solution using an optical system of a confocal microscope or a multiphoton microscope, comprising:
   a light detection region mover which moves a position of a light detection region of the optical system in the sample solution;
   a light detector which detects light from the light detection region; and
   a signal processor which generates time series light intensity data of the light from the light detection region detected with the light detector with moving the position of the light detection region in the sample solution and detects a signal indicating an existence of each single particle individually in the time series light intensity data;
   wherein the light from the light detection region includes substantially constant background light; and the signal indicating an existence of each single particle is a reduction of the light intensity detected with the light detector, which reduction occurs when the single particle enters into the light detection region,
   wherein the signal processor makes the time series light intensity data smoothed, and detects in the smoothed time series light intensity data a downwardly convex, bell-shaped pulse form signal whose intensity is lower than a predetermined threshold value measured from an intensity of the background light as the signal indicating the existence of the single particle.

2. The device of claim 1, wherein the background light is fluorescence, phosphorescence, chemiluminescence, bioluminescence, scattered light owing to substances dispersed in the sample solution or illumination light.

3. The device of claim 1, wherein an emitting light intensity of the single particle is lower than the background light in the detected light wavelength band.

4. The device of claim 1, wherein an outer diameter of the single particle is not less than 15% of a diameter of the light detection region.

5. The device of claim 4, wherein an outer diameter of the single particle is not less than 35% of a diameter of the light detection region.

6. The device of claim 1, wherein the light detection region mover moves the position of the light detection region at a velocity quicker than a diffusion moving velocity of the single particle.

7. The device of claim 1, wherein the light detection region mover moves the position of the light detection region in the sample solution by changing an optical path of the optical system.

8. The device of claim 1, wherein the signal processor judges that one single particle has entered into the light detection region when a signal whose light intensity is lower than a predetermined threshold value measured from an intensity of the background light is detected.

9. The device of claim 1, wherein the signal processor counts a number of the signals indicating the existences of the single particles individually detected during moving the position of the light detection region to count a number of the single particles.

10. The device of claim 1, wherein the signal processor determines a number density or concentration of the single particle in the sample solution based on the number of the detected single particles.

11. The device of claim 1, wherein the moving of the position of the light detection region of the optical system by the light detection region mover, the detecting of the light from the light detection region by the light detector and the detecting of the signals indicating the existences of the single particles by the signal processor are repeated until the number of the signals indicating the existences of the single particles detected with the signal processor reaches a predetermined number; and a concentration of the single particle in the sample solution is determined based on the time taken for the number of the signals indicating the existences of the single particles to reach the predetermined number.

12. A single particle detection method of detecting a single particle dispersed and moving at random in a sample solution using an optical system of a confocal microscope or a multiphoton microscope, comprising:
(a) moving a position of a light detection region of the optical system in the sample solution;
(b) detecting light including substantially constant background light from the light detection region with moving the position of the light detection region in the sample solution, and generating time series light intensity data; and
(c) detecting in the time series light intensity data individually a reduction of an light intensity occurring when the single particle has entered into the light detection region as a signal indicating an existence of each single particle,
wherein, in the step (c), the time series light intensity data is smoothed, and a downwardly convex, bell-shaped pulse form signal whose intensity is lower than a predetermined threshold value measured from an intensity of the background light in the smoothed time series light intensity data is detected as the signal indicating the existence of the single particle.

13. The method of claim 12, wherein the background light is fluorescence, phosphorescence, chemiluminescence, bioluminescence, scattered light owing to substances dispersed in the sample solution or illumination light.

14. The method of claim 12, wherein an emitting light intensity of the single particle is lower than the background light in the detected light wavelength band.

15. The method of claim 12, wherein an outer diameter of the single particle is not less than 15% of a diameter of the light detection region.

16. The method of claim 15, wherein an outer diameter of the single particle is not less than 35% of a diameter of the light detection region.

17. The method of claim 12, wherein, in the step (a), the position of the light detection region is moved at a velocity quicker than a diffusion moving velocity of the single particle.

18. The method of claim 12, wherein, in the step (a), the position of the light detection region in the sample solution is moved by changing an optical path of the optical system.

19. The method of claim 12, wherein, in the step (c), it is judged that one single particle has entered into the light detection region when a signal whose light intensity is lower than a predetermined threshold value measured from an intensity of the background light is detected.

20. The method of claim 12, further comprising (d) counting a number of the signals indicating the existences of the single particles individually detected during moving the position of the light detection region to count a number of the single particles.

21. The method of claim 12, further comprising (e) determining a number density or concentration of the single particle in the sample solution based on the number of the detected single particles.

22. The method of claim 12, repeating until the number of the signals indicating the existences of the single particles reaches a predetermined number the moving of the position of the light detection region of the optical system, the detecting of the light from the light detection region and the detecting of the signals indicating the existences of the single particle; and determining a concentration of the single particle in the sample solution based on the time taken for the number of the signals indicating the existences of the single particles to reach the predetermined number.

23. A computer readable storage device having a computer program product including programmed instructions for single particle detection of detecting light from a single particle dispersed and moving at random in a sample solution using an optical system of a confocal microscope or a multiphoton microscope, said programmed instructions causing a computer to perform steps of:
moving a position of a light detection region of the optical system in the sample solution;
detecting light including substantially constant background light from the light detection region with moving the position of the light detection region in the sample solution, and generating time series light intensity data; and
detecting in the time series light intensity data individually a reduction of a light intensity occurring when the single particle has entered into the light detection region as a signal indicating an existence of each single particle,
wherein, in the procedure of detecting the signal indicating the existence of the single particle individually, the time series light intensity data is smoothed, and a downwardly convex, bell-shaped pulse form signal whose intensity is lower than a predetermined threshold value measured from an intensity of the background light in the smoothed time series light intensity data is detected as the signal indicating the existence of the single particle.

24. The computer readable storage device of claim 23, wherein the background light is fluorescence, phosphorescence, chemiluminescence, bioluminescence, scattered light owing to substances dispersed in the sample solution or illumination light.

25. The computer readable storage device of claim 24, wherein an emitting light intensity of the single particle is lower than the background light in the detected light wavelength band.

26. The computer readable storage device of claims 23, wherein an outer diameter of the single particle is not less than 15% of a diameter of the light detection region.

27. The computer readable storage device of claim 26, wherein an outer diameter of the single particle is not less than 35% of a diameter of the light detection region.

28. The computer readable storage device of claim 23, wherein, in the procedure of moving the position of the light detection region, the position of the light detection region is moved at a velocity quicker than a diffusion moving velocity of the single particle.

29. The computer readable storage device of claim 23, wherein, in the procedure of moving the position of the light detection region, the position of the light detection region in the sample solution is moved by changing an optical path of the optical system.

30. The computer program of claim 23, wherein, in the procedure of detecting the signal indicating the existence of the single particle individually, it is judged that one single particle has entered into the light detection region when a signal whose light intensity is lower than a predetermined threshold value measured from an intensity of the background light is detected.

31. The computer readable storage device of claim 23, further comprising a procedure of counting a number of the signals indicating the existences of the single particles individually detected during moving the position of the light detection region to count a number of the single particles.

32. The computer readable storage device of claim 23, further comprising a procedure of determining a number density or concentration of the single particle in the sample solution based on the number of the detected single particles.

33. The computer readable storage device of claim 23, repeating until the number of the signals indicating the existences of the single particles reaches a predetermined number the moving of the position of the light detection region of the optical system, the detecting of the light from the light detection region and the detecting of the signals indicating the existences of the single particle; and determining a concentration of the single particle in the sample solution based on the time taken for the number of the signals indicating the existences of the single particles to reach the predetermined number.

\* \* \* \* \*